US008012735B2

(12) United States Patent
Balasuriya et al.

(10) Patent No.: US 8,012,735 B2
(45) Date of Patent: Sep. 6, 2011

(54) **INFECTIOUS CDNA CLONE OF THE MODIFIED LIVE VIRUS VACCINE STRAIN OF *EQUINE ARTERITIS* VIRUS**

(75) Inventors: Udeni B. R. Balasuriya, Lexington, KY (US); Peter J. Timoney, Lexington, KY (US); Jianqiang Zhang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 57 days.

(21) Appl. No.: 12/436,242

(22) Filed: May 6, 2009

(65) Prior Publication Data
US 2010/0221826 A1     Sep. 2, 2010

Related U.S. Application Data

(60) Provisional application No. 61/156,595, filed on Mar. 2, 2009.

(51) Int. Cl.
*C12N 7/00*     (2006.01)
*C12N 15/63*     (2006.01)
*C12N 15/85*     (2006.01)

(52) U.S. Cl. ................... 435/235.1; 435/320.1; 435/325

(58) Field of Classification Search .................. None
See application file for complete search history.

(56) References Cited

U.S. PATENT DOCUMENTS

| 6,500,662 | B1 | 12/2002 | Calvert et al. |
| 7,232,680 | B2 | 6/2007 | Calvert et al. |
| 2003/0157689 | A1 | 8/2003 | Calvert et al. |
| 2005/0070700 | A1 | 3/2005 | Giese |
| 2007/0003570 | A1 | 1/2007 | Murtaugh et al. |

OTHER PUBLICATIONS

Balasuriya et al (Journal of General Virology, 2007. vol. 88, pp. 918-924).*
AAT70125 (Sep. 24, 1997 first entry) Equine arteritis virus genome.*
http://vir.sgmjournals.org/cgi/content/abstract/80/8/1949 Journal of General Virology (1999), 80, 1949-1958 © 1999 Society for General Microbiology "Genetic stability of equine arteritis virus during horizontal and vertical transmission in an outbreak of equine viral arteritis" Udeni B. R. Balasuriya, Jodi F. Hedges, Steven A. Nadler, William H. McCollum, Peter J. Timoney and N. James MacLachlan.
http://www.ncbi.nlm.nih.gov/pubmed/17267078 Vaccine; Jul. 26, 2007;25(30):5577-82. Epub Jan. 16, 2007 "Experiences with new generation vaccines against equine viral arteritis, West Nile disease and African horse sickness." MacLachlan NJ, Balasuriya UB, Davis NL, Collier M, Johnston RE, Ferraro GL, Guthrie AJ.
http://jvi.asm.org/cgi/reprint/70/3/1981.pdf Journal of Virology, Mar. 1996, p. 1981-1989 Copyright 1996, American Society for Microbiology "Deduced consensus sequence of Sindbis virus strain AR339: mutations contained in laboratory strains which affect cell culture and in vivo phenotypes" Kevin L. McKnight, Dennis A. Simpson, Seh-Ching Lin, Travis A. Knott, John M. Polo, David F. Pence, Diana B. Johannsen, Hans W. Heidner, Nancy L. Davis, and Robert E. Johnston.
"Development and evolution of three equine vaccines" Bobby O. Moore Irish Veterinary Journal [IR. VET. J.]. vol. 40, No. 5-6, pp. 105-107. 1986.
Zhang, J. et al.; "Equine arteritis virus strain ARVAC, complete genome"; Gen Bank Accession No. EU586275.1 (Aug. 29, 2008).
Balasuriya, U.B., et al.; "Cloning vector pEAVrVBS, complete sequence"; Gen Bank Accession No. DQ846751.1 (Mar. 1, 2007).

* cited by examiner

*Primary Examiner* — Celine Qian
(74) *Attorney, Agent, or Firm* — King & Schickli, PLLC

(57) ABSTRACT

An isolated polynucleotide molecule includes a DNA sequence encoding an infectious RNA molecule encoding a modified live viral strain of an Equine arteritis virus, wherein the DNA sequence is SEQ ID NO:1 or a degenerate variant thereof. Also provided are transformed or transfected host cells including that sequence, vectors including the sequence, and isolated infectious RNA molecules encoded by the sequence. Further, a modified DNA sequence encoding an infectious RNA molecule encoding a modified live viral strain of an Equine arteritis virus is provided wherein the DNA sequence is SEQ ID NO:2 or a degenerate variant thereof, including a silent point mutation allowing distinguishing the modified sequence from the parent and other strains of Equine arteritis virus.

9 Claims, 2 Drawing Sheets

SEQUENCE LISTING

```
<160> NUMBER OF SEQ ID NOS: 18

<210> SEQ ID NO 1
<211> LENGTH: 12704
<212> TYPE: DNA
<213> ORGANISM: Equine arteritis virus

<400> SEQUENCE: 1
gctcgaagtg tgtatggtgc catatacggc tcaccgccat atgcactgca agaattacta      60
ttcttgtggg cccctctcgg taaatcctag agggctttcc tctcgttatt gcgagattcg     120
tcgttagata acggcaagtt ccctttctta ctatcctatt ttcatcttgt ggcttgacgg     180
gtcactgcca tcgtcgtcga tctctatcaa ctacccttgc gactatggca accttctccg     240
ctactggatt tggagggagt tttgttaggg actggtccct ggacttaccc gacgcttgtg     300
agcatggcgc gggattgtgc tgtgaagtgg acggctccac cttatgcgcc gagtgttttc     360
gcggttgcga aggagtggag caatgtcctg gcttgttcat gggactgtta aaactggctt     420
cgccagttcc agtgggacat aagttcctga ttggttggta tcgagctgcc aaagtcaccg     480
```

```
ggcgttacaa tttccttgag ctgttgcaac accctgcttt cgcccagctg cgtgtggttg    540
atgctaggtt agccattgaa gaggcaagtg tgtttatttc cactgaccac gcgtctgcta    600
agcgtttccc tggcgctaga tttgcgctga caccggtgta tgctaacgct tgggttgtga    660
gcccggctgc taacagtttg atagtgacca ctgaccagga acaagatggg ttctgctggt    720 taaaacttt accacctgac cgccgtgagg ctggtttgcg gttgtattac aaccattacc    780
gcgaacaaag gaccgggtgg ctgtctaaaa caggacttcg cttatggctt ggagacctgg    840
gtttgggcat caatgcgagc tctggagggc tgaaattcca cattatgagg ggttcgcctc    900
agcgagcttg gcatatcaca acacgcagct gcaagctgaa gagctactac gtttgtgaca    960
tctctgaagc agactggtcc tgtttgcccg ctggcaacta cggcggctac aatccaccag   1020
gggacggagc ttgcggttac aggtgcttgg ccttcatgaa tggcgccact gttgtgtcgg   1080
ctggttgcag ttctgacttg tggtgtgatg atgagttggc ttatcgagtc tttcaattgt   1140
cacccacgtt cacggttacc atcccaggtg ggcgagtttg tccgaatgcc aagtacgcaa   1200
tgatttgtga caagcagcac tggcgcgtca aacgtgcaaa gggcgtcggc ctgtgtctcg   1260
atgaaagctg tttcaggggc acctgcaatt gccaacgcat gagtggacca ccacctgcac   1320
ccgtgtcagc cgccgtgtta gatcacatac tggaggcggc gacgtttggc aacgttcgcg   1380
tggttatacc tgaagggcag ccacgccccg taccagcgcc gcgagttcat ccctgcgcca   1440
actcttctgg agatgtcaaa gatccggcgc ccgttccgcc agtaccaaaa ccaaggacca   1500
agcttgccaa accgaaccca actcaggcgc ccatcccagc accgcgcacg cgacttcaag   1560
gggcctcaac acaggagcca ctggcgagtg cgggagttgc ttctgactcg gcacccaaat   1620
ggcgtgtggc caaaactgtg tacagctccg cggagcgctt tcggaccgaa ctggtacaac   1680
gtgctcggtc cgttggggac gttcttgttc aagcgctacc gcacaaaacc ccagcagtgc   1740
agcggtatac catgactctg aagatgatgc gttcacgctt cagttggcac tgcgacatgt   1800 ggtaccctt ggctgtaatc gcttgtttgc tcccccatatg gccatctctt gctttgctcc    1860
ttagcttcgc cattgggttg atacccagtg tgggcaataa tgttgttctg acagcgcttc   1920
tggtttcatc agctaattat gttgcgtcaa tggaccatca ctgtgaaggt gcggcttgct   1980
tagccttgct ggaagaagaa cactattata gagcggtccg ttggcgcccg attacaggcg   2040
cgctgtcgct tgtgctcaat ttactggggc aggtaggcta tgtagctcgt tccacctttg   2100
atgcagctta tgttccttgc actgtgttcg atctttgcag cttttgctatt ctgtacctct   2160 gctgcaatcg ttgctggaga tgcttcggac gctgtgtgcg agtgggcct gccacgcatg    2220 ttttgggttc caccgggcaa cgagtttcca aactggcgct cattgatttg tgtgaccact   2280
tttcaaagcc caccatcgac gttgtgggca tggcaactgg ttggagcgga tgttacacag   2340
gaaccgccgc aatggagcgt cagtgtgcct ctacggtgga ccctcactcg ttcgaccaga   2400
agaaggcagg agcgattgtt tacctcaccc ccctgtcaa cagcgggtct gcgctgcagt     2460
gcctcaatgt catgtggaag cgaccaattg ggtccactgt ccttggggaa caaacaggag   2520
ctgttgtgac ggcggtcaag agcatctctt tctcacctcc ctgctgcgtc tctaccactt    2580 tgccacccg accggtgtg accgttgtcg accatgctct ttacaaccgg ttgactgctt     2640
caggggtcga tcccgcttta ttgcgtgttg ggcaaggtga ttttctaaaa cttaatccgg   2700
ggttccggct gataggtgga tggatttatg ggatatgcta ttttgtgttg gtggttgtgt    2760 caactttac ctgcctacct atcaaatgtg gcattggcac ccgcgaccct ttctgccgca    2820
gagtgttttc tgtacccgtc atcaagaccc aagagcactg ccatgctgga atgtgtgcta   2880
```

```
gcgctgaagg catctctctg gactctctgg ggttaactca gttacaaagt tattggatcg   2940
cagccgtcac tagcggatta gtgatcttgt tggtctgcca ccgcctggcc atcagcgcct   3000
tggacttgtt gactctagct tcccctttag tgttgcttgt gttcccttgg catctgtgg    3060 ggcttttact tgcttgcagt ctcgctggtg ctgctgtgaa aatacagttg ttggcgacgc   3120
tttttgtgaa tctgttcttt ccccaagcta cccttgtcac tatgggatac tgggcgtgcg   3180
tggcggcttt ggccgtttac agtttgatgg gcttgcgagt gaaagtgaat gtgcccatgt   3240
gtgtgacacc tgcccatttt ctgctgctgg cgaggtcagc tggacagtca agagagcaga   3300
tgctccgggt cagcgctgct gcccccacca attcactgct tggagtggct cgtgattgtt   3360
atgtcacagg cacaactcgg ctgtatatac ccaaggaagg cgggatggtg tttgaagggc   3420
tattcaggtc accgaaggcg cgcggcaacg tcggcttcgt ggctggtagc agctacggca   3480
cagggtcagt gtggaccagg aacaacgagg tcgtcgtact gacagcgtca cacgtggttg   3540
gccgcgctaa catggccact ctgaagatcg gtgacgcaat gctgactctg actttcaaaa   3600
aaaatggcga cttcgccgag gcagtgacga cacagtccga gctcccaggc aattggccac   3660
agttgcattt cgcccaacca acaaccgggc ccgcttcatg gtgcactgcc acaggagatg   3720
aagaaggctt gctcagtggc gaggtttgtc tggcgtggac tactagtggc gactctggat   3780
cagcagtggt tcagggtgac gctgtggtag gggtccacac cggttcgaac acaagtggtg   3840
ttgcctacgt gaccaccccca gcggaaaaac tccttggcgc cgacaccgtg actttgtcgt   3900
cactgtcaaa gcatttcaca ggccctttga catcaatccc gaaggacatc cctgacaaca   3960
tcattgccga tgttgatgct gttcctcgtt ctctggccat gctgattgat ggcttatcta   4020
atagagagag cagcctttct ggacctcagt tgttgttaat tgcttgtttt atgtggtctt   4080
atcttaacca acctgcctac ttgccttatg tgctgggctt ctttgccgct aacttcttcc   4140
tgccaaaaag tgttggccgc cctgtggtca ctgggcttct atggttgtgc tgcctcttca   4200
caccgctttc catgcgcttg tgcttgttcc atctggtctg tgctaccgtc acgggaaacg   4260
tgatatcttt gtggttctac atcactgccg ctggcacgtc ttacctttct gagatgtggt   4320
tcggaggcta tcccaccttg ttgtttgtgc cacggttcct agtgtaccag ttccccggct   4380
gggctattgg cacagtacta gcggtatgca gcatcaccat gctggctgct gccctcggtc   4440
acaccctgtt actggatgtg ttctccgcct cgggtcgctt tgacaggact ttcatgatga   4500
aatacttcct ggagggagga gtgaaagaga gtgtcaccgc ctcagtcacc cgcgcttatg   4560
gcaaaccaat tacccaggag agtctcactg caacattagc tgccctcact gatgatgact   4620
tccaattcct ctctgatgtg cttgactgtc gggccgtccg atcggcaatg aatctgcgtg   4680
ccgctctcac aagttttcaa gtggcgcagt atcgtaacat ccttaatgca tccttgcaag   4740
tcgatcgtga cgctgctcgt agtcgcagac taatggcaaa actggctgat tttgcggttg   4800
aacaagaagt aacagccgga gaccgtgttg ttgttatcga cggtctggac cgcatggctc   4860
acttcaaaga cgatttggtg ctggttcctt tgaccaccaa agtagtaggc ggttctaggt   4920
gcaccatttg tgacgtcgtt aaggaagaag ccaatgacac cccagttaag ccaatgccca   4980
gcaggagacg ccgcaagggc ctgcctaaag tgctcagtt ggagtgggac cgtcaccagg   5040
aagagaagag gaacgccggt gatgatgatt ttgcggtctc gactgattat gtcaagagag   5100
tgccaaagta ctgggatccc agcgacaccc gaggcacgac agtgaaaatc gccggcacta   5160
cctatcagaa agtggttgac tattcaggca atgtgcatta cgtggagcat caggaagatc   5220
tgctagacta cgtgctgggc aaggggagct atgaaggcct agatcaggac aaagtgttgg   5280
```

```
acctcacaaa catgcttaaa gtggacccca cggagctctc ctccaaagac aaagccaagg    5340
cgcgtcagct tgctcatctg ctgttggatc tggctaaccc agttgaggca gtgaatcagt    5400
taaactgaga gcgccccaca tctttcccgg cgatgtgggg cgtcggacat ttgctgactc    5460
taaagacaag ggtttcgtgg ctctacacag tcgcacaatg ttttttagctg cccgggactt   5520 tttatttaac atcaaatttg tgtgcgacga agagttcaca aagacccaa aagacacact    5580 gcttgggtac gtacgcgcct gccctggtta ctggtttatt ttccgtcgta cgcaccggtc    5640
actgattgat gcatactggg acagtatgga gtgcgtttac gcgcttccca ccatatctga    5700
ttttgatgtg agcccaggtg acgtcgcagt gacgggtgag cgatgggatt ttgaatctcc    5760
cggaggaggc cgtgcaaaac gtctcacagc tgatctggtg cacgcttttc aagggttcca    5820
cggagcctct tattcctatg atgacaaggt ggcagctgct gtcagtggtg acccgtatcg    5880
gtcggacggc gtcttgtata caccccgttg gggcaacatt ccatattctg tcccaaccaa    5940
tgctttggaa gccacagctt gctaccgtgc tggatgtgag gccgttaccg acgggaccaa    6000
cgtcatcgca acaattgggc ccttcccgga gcaacaaccc ataccggaca tcccaaagag    6060
cgtgcttgac aactgcgctg acatcagctg tgacgctttc atagcgcccg ctgcagagac    6120
agccctgtgt ggtgatttag agaaatacaa cctatccacg cagggttttg tgttgcctag    6180
tgttttctcc atggtgcggg cgtacttaaa gaggagatt ggagcgctc caccactcta     6240 cttgccatct actgtaccat ctaaaaattc acaagccgga attaacggcg ctgagtttcc    6300
tacaaggtct ttacagagct actgtttgat tgatgacatg gtgtcacagt ccatgaaaag    6360
caatctacaa accgccacca tggcgacttg taaacggcag tactgttcca aatacaagat    6420
taggagcatt ctgggcacca acaattacat tggcctaggt ttgcgtgcct gcctttcggg    6480
ggttacggcc gcattccaaa agctggaaa ggatgggtca ccgatttatt tgggcaagtc     6540
aaaattcgac ccgatacctg ctcctgacaa gtactgcctt gaaacagacc tggagagttg    6600
tgatcgctcc accccggctt tggtgcgttg gttcgctact aatcttatt ttgagctagc     6660 tggccagccc gagttggtgc acagctacgt gttgaattgc tgtcacgatc tagttgtggc    6720
aggtagtgta gcattcacca aacgcggggg tttgtcatct ggagacccta tcacttccat    6780
ttccaatacc atctattcat tggtgctgta cacccagcac atgttgctat gtggacttga    6840
aggctatttc ccagagattg cagaaaaata tcttgatggc agcctggagc tgcgggacat    6900
gttcaagtac gttcgagtgt acatctactc ggacgatgtg gttctaacca cacccaacca    6960
gcattacgcg gccagctttg accgctgggt cccccacctg caggcgctgc taggtttcaa    7020
ggttgaccca agaaaaactg tgaacaccag ctcccctccc tttttgggct gccggttcaa    7080
gcaagtggac ggcaagtgtt atctggccag tcttcaggac cgcgttacac gctctctgtt    7140
ataccacatt ggtgcaaaga atccctcaga gtactatgaa gctgctgttt ccatctttaa    7200
ggactccatt atctgctgtg atgaagattg gtggacggac ctccatcgac gtatcagtgg    7260
cgctgcgcgt actgacggag ttgagttccc caccattgaa atgttaacat ccttccgcac    7320
caagcagtat gagagtgccg tgtgcacagt ttgtggggcc gccccgtgg ccaagtctgc     7380 ttgtggaggg tggttctgtg gcaattgtgt cccgtaccac gtgggtcatt gtcacacaac    7440
ctcgctcttc gccaactgcg ggcacgacat catgtaccgc tccacttact gcacaatgtg    7500
tgagggttcc ccaaaacaga tggtaccaaa agtgcctcac ccgatcctgg atcatttgct    7560
gtgccacgtt gattacggca gtaaagagga actaactctg gtagtggcgg atggtcgaac    7620
aacatcaccg cccgggcgct acaaagtggg tcacaaggta gtcgccgtgg ttgcagacgt    7680
```

```
gggaggcaac attgtgtttg ggtgcggtcc tggatcacac atcgcagtac cacttcagga    7740
tacgctcaag ggcgtggtgg tgaataaagc tctgaagaac gccgccgcct ctgagtacgt    7800
ggaaggaccc cctgggagtg ggaagacttt tcacctggtc aaagatgtgc tagccgtggt    7860
cggtagcgcg accttggttg tgcccaccca cgcgtccatg ctggactgca ttaacaagct    7920
caaacaagcg ggcgccgatc catactttgt ggtgcccaag tatacagttc ttgactttcc    7980
ccggcctggc agtggaaaca tcacagtgcg actgccacag gtcggaacta gtgagggaga    8040
aacctttgtg gatgaggtgg cttacttctc accagtggat ctggcgcgca tttttaaccca   8100 gggtcgagtc aagggttacg gtgatttaaa tcagctcggg tgcgtcggac ccgcgagcgt    8160
gccacgtaac cttggctcc gacattttgt cagcctggag cccttgcgag tgtgccatcg    8220
attcggcgct gctgtgtgtg atttgatcaa gggcatttat ccttattatg agccagctcc    8280
acataccact aaagtggtgt tgtgccaaa tccagacttt gagaaaggtg tagtcatcac    8340
cgcctaccac aaagatcgcg gtcttggtca ccgcacaatt gattcaattc aaggctgtac    8400
attccctgtt gtgactcttc gactgccac accccaatca ctgacgcgcc cgcgcgcagt    8460
tgtggcggtt actagggcgt ctcaggaatt atacatctac gacccctttg atcagcttag    8520
cgggttgttg aagttcacca aggaagcaga ggcgcaggac ttgatccacg gcccacctac    8580
agcatgccac ctgggccaag aaattgacct ttggtccaat gagggcctcg aatattacaa    8640
ggaagtcaac ctgctgtaca cacacgtccc catcaaggat ggtgtaatac acagttaccc    8700
taattgtggc cctgcctgtg gctgggaaaa gcaatccaac aaaatttcgt gcctcccgag    8760
agtggcacaa aatttgggct accactattc cccagatttta ccaggatttt gccccatacc    8820
gaaagaactc gctgagcatt ggcccgtagt gtccaatgat agatacccga attgcttgca    8880
aattacctta cagcaagtat gtgaactcag taaaccgtgc tcagcgggct atatggttgg    8940
acaatctgtt ttcgtgcaga cgcctggtgt gacatcttac tggcttactg aatgggtcga    9000
cggcaaagcg cgtgctctac cagattcctt attctcgtcc ggtaggttcg agactaacag    9060
ccgcgttttc ctcgatgaag ccgaggaaaa gtttgccgcc gctcaccctc atgcctgttt    9120
gggagaaatt aataagtcca ccgtgggagg atcccacttc atcttttccc aatatttacc    9180
accactgcta cccgcaggcg ctgttgccct ggtaggtgct tcattggctg ggaaagctgc    9240
taaagctgct tgcagcgttg ttgatgtcta tgctccatcg ttgaaccctt atctacaccc    9300
tgagacactg agtcgcgtgt acaagattat gatcgatttc aagccgtgta ggcttatggt    9360
gtggagaaac gcgacctttt atgtccaaga gggtgttgat gcagttacat cagcactagc    9420
agctgtgtcc aaactcatca aagtgccggc caatgagcct gtttcattcc atgtggcatc    9480
agggtacaga accaacgcgc tggtagcgcc ccaggctaaa atttcaattg gagcctacgc    9540
cgccgagtgg gcactgtcaa ctgaaccgcc accggctggt tatgcgatcg tgcggcgata    9600
tattgtaaag aggctcctca gctcaacaga agtgttcttg tgccgcaggg gtgttgtgtc    9660
ttccacctca gtgcagacca tttgtgcact agagggatgt aaacctctgt tcaacttctt    9720
acaaattggt tcagtcattg ggcccgtgtg atgggctag tgtggtcact gatttcaaat    9780
tctattcaga ctattattgc tgatttttgct atttctgtga ttgatgcagc gcttttcttt    9840
ctcatgctac ttgcattggc tgttgttact gtgtttcttt tctggctcat tgttgccatc    9900
ggccgcagct tggtggcgcg tgttcacga ggtgcgcgtt acagacctgt ttaaggattt    9960
gcagtgcgac aacctgcgcg cgaaagatgc cttcccgagt ctgggacatg ctctgtcgat   10020
tggccagtcg aggctatcgt atatgctgca ggattggttg cttgctgcgc accgcaagga   10080
```

```
agttatgcct tccaatacca tgcctatgcc cggtcttact cctgattgct ttgaccatct    10140
ggagtcttct agctatgctc catttatcaa tgcctatcgg caggcaattt tgagtcaata    10200
ctcacaagag ctcctgctcg aagccatcaa ctgtaaattg cttgctgtgg ttgcaccggc    10260
attgtatcac aattaccatc tagccaattt gaccgaaccg gccacatggg tcgtgcctac    10320
agtgggccag ttgcactatt atgcttcttc ctctattttt gcttcatctg tggaagtgtt    10380
ggcagcaata atactactat ttgcatgcat accactagtg cacgagtgt acatctcttt    10440 tacgcggcta atgtcacctt cccgtcgcac ttccagcggc actttgccgc cgcgcaagat    10500
tttgtagtgc acacgggtta tgaatatgcc ggggtcacta tggtagtgca cttgtttgcc    10560
aacttggttc tgacatttcc gagcttagtt aattgttccc gccctgtgaa tgtcttttgct    10620 aatgcttctt gcgtgcaagt ggtttgtagt cataccaact caactactgg ctcgggtcaa    10680
cttccgtttt cctttgtaga tgaagatctc cggctgcata tcaggcctac tcttatttgt    10740
tggtttgcct tgttgttggt gcactttcta cccatgccac gctacagagg ctcgcaattt    10800
tacttacact agtcatggat tgggccacgt gcacggtcat gaggggtgta ggaattttat    10860
taatgtcact cattctgcat ttctttatct taatcccacc actctcactg cgccggctat    10920
aactcattgt ttacttctgg ttctggcagc caaaatggaa cacccaaacg ctactatctg    10980
gctgcagctg cagccgtttg ggtatcatgt ggctggcgat gtcattgtca acttggaaga    11040
gaataagagg catccttact ttaaactctt gagagcgccg gctttaccgc ttggttttgt    11100
ggctatagtt tatgttcttt tacgactggt acgttgggct caacaatgct atctatgatt    11160
gtattgttat tcttgctttg gggtgcgcca tcacatgctt acttctcata ctacaccgct    11220
cagcgcttca cagacttcac cttgtgcatg ctgacggatc gcggcgttat tgccaatttg    11280
ctgcgatatg atgagcacac tgctttgtac aattgttccg ccagtaaaac ctgttggtat    11340
tgcacattcc cggacgaaaa gattatcacg tttggaaccg attgtgatga cacctacgcg    11400
gtcccagttg ctgaggtcct ggaacaggcg catggaccgt acggtgtgct gtttggtgac    11460
gtgccccctt ttatttacta tggccgtgaa ttcggcatag ttgtgttgga tgtgtttatg    11520
ttctatcccg ttttagttct gttttttctta tcagtactac cctatgctac gcttattctt    11580
gaaatgtgtg tatctattct gtttataatc tatggcattt acagcggggc ctacttggcc    11640
atgggcatat tttcggccac gcttgctata cattcaattg tggtcctccg ccaattactg    11700
tggttatgcc tggcttggcg ataccgctgc acgcttcacg cgtccttat atcagctgag    11760 gggaaagtgt accccgtaga ccccgaactc ccggttgccg ccgcgggcaa tcggttgcta    11820
gtcccaggta ggcccactat cgattatgca gtggcctacg gcagcaaagt caaccttgtg    11880
aggttggggg cagctgaggt atgggagcca tagattcatt ttgtggtgac gggatttag    11940 gtgagtatct agattacttt attctgtccg tcccactctt gctgttgctt actaggtatg    12000
tagcatctgg gtcagtgtat gttttgactg ccttgttcta ttccttagta ttagcagctt    12060
atatttggtt tgtcatagtt ggaagagcct tttccactgc ttatgctttt gcgcttttgg    12120
ctgcttttct gttattagta acgaggatga ttgtaggtat gatgcctcgt cttcggtcca    12180
ttttcaacca tcgccaactg gtggtagctg attttgtgga cacacctagt ggacctgttc    12240 ccatccccg ctcaactact caggtagtgg ttcgcggcaa cgggtacacc gcagttggta    12300
acaagcttgt cgatggcgtc aagacgatca cgtccgcagg ccgcctctgt tcgaaacgga    12360
tggcggcgac agcctacaag ctacaatgac ctactgcgca tgtttggtca gatgcgggtc    12420
cgcaaaccgc ccgcgcaacc cactcaggct attattgcag agcctggaga ccttaggcat    12480
```

```
gatttaaatc aacaggagcg cgccacccct tcgtcgaacg tacaacggtt cttcatgatt    12540
gggcatggtt cactcactgc agatgccgga ggactcacgt acaccgtcag ttgggttcct    12600
accaaacaaa tccagcgcaa aattgcgcct ccagcagggc cgtaagacgt ggatattctc    12660
ctgtgtggcg tcatgttgaa gtagttatta gccacccagg aacc                     12704

<210> SEQ ID NO 2
<211> LENGTH: 12704
<212> TYPE: DNA
<213> ORGANISM: Equine arteritis virus

<400> SEQUENCE: 2
gctcgaagtg tgtatggtgc catatacggc tcaccgccat atgcactgca agaattacta      60
ttcttgtggg cccctctcgg taaatcctag agggctttcc tctcgttatt gcgagattcg     120
tcgttagata acggcaagtt ccctttctta ctatcctatt ttcatcttgt ggcttgacgg     180
gtcactgcca tcgtcgtcga tctctatcaa ctacccttgc gactatggca accttctccg     240
ctactggatt tggagggagt tttgttaggg actggtccct ggacttaccc gacgcttgtg     300
agcatggcgc gggattgtgc tgtgaagtgg acggctccac cttatgcgcc gagtgttttc     360
gcggttgcga aggagtggag caatgtcctg gcttgttcat gggactgtta aaactggctt     420
cgccagttcc agtgggacat aagttcctga ttggttggta tcgagctgcc aaagtcaccg     480
ggcgttacaa tttccttgag ctgttgcaac accctgcttt cgcccagctg cgtgtggttg     540
atgctaggtt agccattgaa gaggcaagtg tgtttatttc cactgaccac gcgtctgcta     600
agcgtttccc tggcgctaga tttgcgctga caccggtgta tgctaacgct tgggttgtga     660
gcccggctgc taacagtttg atagtgacca ctgaccagga acaagatggg ttctgctggt     720
taaaactttt accacctgac cgccgtgagg ctggtttgcg gttgtattac aaccattacc     780
gcgaacaaag gaccgggtgg ctgtctaaaa caggacttcg cttatggctt ggagacctgg     840
gtttgggcat caatgcgagc tctggagggc tgaaattcca cattatgagg ggttcgcctc     900
agcgagcttg gcatatcaca acacgcagct gcaagctgaa gagctactac gtttgtgaca     960
tctctgaagc agactggtcc tgtttgcccg ctggcaacta cggcggctac aatccaccag    1020
gggacggagc ttgcggttac aggtgcttgg ccttcatgaa tggcgccact gttgtgtcgg    1080
ctggttgcag ttctgacttg tggtgtgatg atgagttggc ttatcgagtc tttcaattgt    1140
cacccacgtt cacggttacc atcccaggtg ggcgagtttg tccgaatgcc aagtacgcaa    1200
tgatttgtga caagcagcac tggcgcgtca aacgtgcaaa gggcgtcggc ctgtgtctcg    1260
atgaaagctg tttcagggc acctgcaatt gccaacgcat gagtggacca ccacctgcac    1320
ccgtgtcagc cgccgtgtta gatcacatac tggaggcggc gacgtttggc aacgttcgcg    1380
tggttatacc tgaagggcag ccacgccccg taccagcgcc gcgagttcat ccctgcgcca    1440
actcttctgg agatgtcaaa gatccggcgc ccgttccgcc agtaccaaaa ccaaggacca    1500
agcttgccaa accgaaccca actcaggcgc ccatcccagc accgcgcacg cgacttcaag    1560
gggcctcaac acaggagcca ctggcgagtg cgggagttgc ttctgactcg gcacccaaat    1620
ggcgtgtggc caaaactgtg tacagctccg cggagcgctt tcggaccgaa ctggtacaac    1680
gtgctcggtc cgttggggac gttcttgttc aagcgctacc gcacaaaacc ccagcagtgc    1740
agcggtatac catgactctg aagatgatgc gttcacgctt cagttggcac tgcgacatgt    1800 ggtaccctt ggctgtaatc gcttgtttgc tccccatatg gccatctctt gctttgctcc    1860
ttagcttcgc cattgggttg ataccagtg tgggcaataa tgttgttctg acagcgcttc    1920
```

```
tggtttcatc agctaattat gttgcgtcaa tggaccatca ctgtgaaggt gcggcttgct    1980
tagccttgct ggaagaagaa cactattata gagcggtccg ttggcgcccg attacaggcg    2040
cgctgtcgct tgtgctcaat ttactggggc aggtaggcta tgtagctcgt tccacctttg    2100
atgcagctta tgttccttgc actgtgttcg atctttgcag ctttgctatt ctgtacctct    2160
gctgcaatcg ttgctggaga tgcttcggac gctgtgtgcg agtttgggcct gccacgcatg   2220
ttttgggttc caccgggcaa cgagtttcca aactggcgct cattgatttg tgtgaccact    2280
tttcaaagcc caccatcgac gttgtgggca tggcaactgg ttggagcgga tgttacacag    2340
gaaccgccgc aatggagcgt cagtgtgcct ctacggtgga ccctcactcg ttcgaccaga    2400
agaaggcagg agcgattgtt tacctcaccc ccctgtcaa cagcgggtct gcgctgcagt     2460
gcctcaatgt catgtggaag cgaccaattg ggtccactgt ccttgggaa caaacaggag     2520
ctgttgtgac ggcggtcaag agcatctctt tctcacctcc ctgctgcgtc tctaccactt    2580
tgcccacccg accggtgtg accgttgtcg accatgctct ttacaaccgg ttgactgctt     2640
caggggtcga tcccgcttta ttgcgtgttg ggcaaggtga ttttctaaaa cttaatccgg    2700
ggttccggct gataggtgga tggatttatg ggatatgcta ttttgtgttg gtggttgtgt    2760
caacttttac ctgcctacct atcaaatgtg gcattggcac ccgcgaccct ttctgccgca    2820
gagtgttttc tgtacccgtc atcaagaccc aagagcactg ccatgctgga atgtgtgcta    2880
gcgctgaagg catctctctg gactctctgg ggttaactca gttacaaagt tattggatcg    2940
cagccgtcac tagcggatta tgatcttgt tggtctgcca ccgcctggcc atcagcgcct    3000
tggacttgtt gactctagct tccccttag tgttgcttgt gttcccttgg gcatctgtgg    3060
ggcttttact tgcttgcagt ctcgctggtg ctgctgtgaa aatacagttg ttggcgacgc    3120
tttttgtgaa tctgttctt ccccaagcta cccttgtcac tatgggatac tgggcgtgcg    3180
tggcggcttt ggccgtttac agtttgatgg gcttgcgagt gaaagtgaat gtgcccatgt    3240
gtgtgacacc tgcccatttt ctgctgctgg cgaggtcagc tggacagtca agagagcaga    3300
tgctccgggt cagcgctgct gcccccacca attcactgct tggagtggct cgtgattgtt    3360
atgtcacagg cacaactcgg ctgtatatac ccaaggaagg cgggatggtg tttgaagggc    3420
tattcaggtc accgaaggcg cgcggcaacg tcggcttcgt ggctggtagc agctacggca    3480
cagggtcagt gtggaccagg aacaacgagg tcgtcgtact gacagcgtca cacgtggttg    3540
gccgcgctaa catggccact ctgaagatcg gtgacgcaat gctgactctg actttcaaaa    3600
aaaatggcga cttcgccgag gcagtgacga cacagtccga gctcccaggc aattggccac    3660
agttgcattt cgcccaacca caaccgggc ccgcttcatg gtgcactgcc acaggagatg     3720
aagaaggctt gctcagtggc gaggtttgtc tggcgtggac tactagtggc gactctggat    3780
cagcagtggt tcagggtgac gctgtggtag gggtccacac cggttcgaac acaagtggtg    3840
ttgcctacgt gaccaccccca agcggaaaac tccttggcgc cgacaccgtg actttgtcgt   3900
cactgtcaaa gcatttcaca ggccctttga catcaatccc gaaggacatc cctgacaaca    3960
tcattgccga tgttgatgct gttcctcgtt ctctggccat gctgattgat ggcttatcta    4020
atagagagag cagcctttct ggacctcagt tgttgttaat tgcttgtttt atgtggtctt    4080
atcttaacca acctgcctac ttgccttatg tgctgggctt ctttgccgct aacttcttcc    4140
tgccaaaaag tgttggccgc cctgtgggtca ctgggcttct atggttgtgc tgcctcttca   4200
caccgctttc catgcgcttg tgcttgttcc atctggtctg tgctaccgtc acgggaaacg    4260
tgatatcttt gtggttctac atcactgccg ctggcacgtc ttacctttct gagatgtggt    4320
```

```
tcggaggcta tcccaccttg ttgtttgtgc cacggttcct agtgtaccag ttccccggct    4380
gggctattgg cacagtacta gcggtatgca gcatcaccat gctggctgct gccctcggtc    4440
acaccctgtt actggatgtg ttctccgcct cgggtcgctt tgacaggact ttcatgatga    4500
aatacttcct ggagggagga gtgaaagaga gtgtcaccgc ctcagtcacc cgcgcttatg    4560
gcaaaccaat tacccaggag agtctcactg caacattagc tgccctcact gatgatgact    4620
tccaattcct ctctgatgtg cttgactgtc gggccgtccg atcggcaatg aatctgcgtg    4680
ccgctctcac aagttttcaa gtggcgcagt atcgtaacat ccttaatgca tccttgcaag    4740
tcgatcgtga cgctgctcgt agtcgcagac taatggcaaa actggctgat tttgcggttg    4800
aacaagaagt aacagccgga gaccgtgttg ttgttatcga cggtctggac cgcatggctc    4860
acttcaaaga cgatttggtg ctggttcctt tgaccaccaa agtagtaggc ggttctaggt    4920
gcaccatttg tgacgtcgtt aaggaagaag ccaatgacac cccagttaag ccaatgccca    4980
gcaggagacg ccgcaagggc ctgcctaaag gtgctcagtt ggagtgggac cgtcaccagg    5040
aagagaagag gaacgccggt gatgatgatt ttgcggtctc gactgattat gtcaagagag    5100
tgccaaagta ctgggatccc agcgacaccc gaggcacgac agtgaaaatc gccggcacta    5160
cctatcagaa agtggttgac tattcaggca atgtgcatta cgtggagcat caggaagatc    5220
tgctagacta cgtgctgggc aaggggagct atgaaggcct agatcaggac aaagtgttgg    5280
acctcacaaa catgcttaaa gtgaccccca cggagctctc ctccaaagac aaagccaagg    5340
cgcgtcagct tgctcatctg ctgttggatc tggctaaccc agttgaggca gtgaatcagt    5400
taaactgaga gcgccccaca tctttcccgg cgatgtgggg cgtcggacat tgctgactc    5460 taaagacaag ggtttcgtgg ctctacacag tcgcacaatg ttttttagctg cccgggactt    5520 tttatttaac atcaaatttg tgtgcgacga agagttcaca aagaccccaa aagacacact    5580
gcttgggtac gtacgcgcct gccctggtta ctggtttatt ttccgtcgta cgcaccggtc    5640
actgattgat gcatactggg acagtatgga gtgcgtttac gcgcttccca ccatatctga    5700
ttttgatgtg agcccaggtg acgtcgcagt gacgggtgag cgatgggatt ttgaatctcc    5760
cggaggaggc cgtgcaaaac gtctcacagc tgatctggtg cacgcttttc aagggttcca    5820
cggagcctct tattcctatg atgacaaggt ggcagctgct gtcagtggtg acccgtatcg    5880
gtcggacggc gtcttgtata acacccgttg gggcaacatt ccatattctg tcccaaccaa    5940
tgctttggaa gccacagctt gctaccgtgc tggatgtgag gccgttaccg acgggaccaa    6000
cgtcatcgca acaattgggc ccttcccgga gcaacaaccc ataccggaca tcccaaagag    6060
cgtgcttgac aactgcgctg acatcagctg tgacgctttc atagcgcccg ctgcagagac    6120
agccctgtgt ggtgatttag agaaatacaa cctatccacg cagggttttg tgttgcctag    6180
tgttttctcc atggtgcggg cgtacttaaa agaggagatt ggagacgctc caccactcta    6240
cttgccatct actgtaccat ctaaaaattc acaagccgga attaacggcg ctgagtttcc    6300
tacaaggtct ttacagagct actgtttgat tgatgacatg gtgtcacagt ccatgaaaag    6360
caatctacaa accgccacca tggcgacttg taaacggcag tactgttcca aatacaagat    6420
taggagcatt ctgggcacca acaattacat tggcctaggt ttgcgtgcct gcctttcggg    6480
ggttacggcc gcattccaaa aagctggaaa ggatgggtca ccgatttatt tgggcaagtc    6540
aaaattcgac ccgatacctg ctcctgacaa gtactgcctt gaaacagacc tggagagttg    6600
tgatcgctcc accccggctt tggtgcgttg gttcgctact aatcttattt ttgagctagc    6660
tggccagccc gagttggtgc acagctacgt gttgaattgc tgtcacgatc tagttgtggc    6720
```

```
aggtagtgta gcattcacca aacgcggggg tttgtcatct ggagaccota tcacttccat    6780
ttccaatacc atctattcat tggtgctgta cacccagcac atgttgctat gtggacttga    6840
aggctatttc ccagagattg cagaaaaata tcttgatggc agcctggagc tgcgggacat    6900
gttcaagtac gttcgagtgt acatctactc ggacgatgtg gttctaacca cacccaacca    6960
gcattacgcg gccagctttg accgctgggt cccccacctg caggcgctgc taggtttcaa    7020
ggttgaccca agaaaaactg tgaacaccag ctccccttcc ttttttgggct gccggttcaa    7080
gcaagtggac ggcaagtgtt atctggccag tcttcaggac cgcgttacac gctctctgtt    7140
ataccacatt ggtgcaaaga atccctcaga gtactatgaa gctgctgttt ccatctttaa    7200
ggactccatt atctgctgtg atgaagattg tggacggac ctccatcgac gtatcagtgg     7260
cgctgcgcgt actgacggag ttgagttccc caccattgaa atgttaacat ccttccgcac    7320
caagcagtat gagagtgccg tgtgcacagt ttgtggggcc gcccccgtgg ccaagtctgc    7380
ttgtggaggg tggttctgtg gcaattgtgt cccgtaccac gtgggtcatt gtcacacaac    7440
ctcgctcttc gccaactgcg ggcacgacat catgtaccgc tccacttact gcacaatgtg    7500
tgagggttcc ccaaaacaga tggtaccaaa agtgcctcac ccgatcctgg atcatttgct    7560
gtgccacgtt gattacggca gtaaagagga actaactctg gtagtggcgg atggtcgaac    7620
aacatcaccg cccgggcgct acaaagtggg tcacaaggta gtcgccgtgg ttgcagacgt    7680
gggaggcaac attgtgtttg ggtgcggtcc tggatcacac atcgcagtac cacttcagga    7740
tacgctcaag ggcgtggtgg tgaataaagc tctgaagaac gccgccgcct ctgagtacgt    7800
ggaaggaccc cctgggagtg ggaagacttt tcacctggtc aaagatgtgc tagccgtggt    7860
cggtagcgcg accttggttg tgcccaccca cgcgtccatg ctggactgca ttaacaagct    7920
caaacaagcg ggcgccgatc catactttgt ggtgcccaag tatacagttc ttgactttcc    7980
ccggcctggc agtggaaaca tcacagtgcg actgccacag gtcggaacta gtgagggaga    8040
aacctttgtg gatgaggtgg cttacttctc accagtggat ctggcgcgca ttttaaccca    8100
gggtcgagtc aagggttacg gtgatttaaa tcagctcggg tgcgtcggac ccgcgagcgt    8160
gccacgtaac cttggctcc gacattttgt cagcctggag cccttgcgag tgtgccatcg     8220
attcggcgct gctgtgtgtg atttgatcaa gggcatttat ccttattatg agccagctcc    8280
acataccact aaagtggtgt tgtgtgccaaa tccagacttt gagaaaggtg tagtcatcac   8340
cgcctaccac aaagatcgcg gtcttggtca ccgcacaatt gattcaattc aaggctgtac    8400
attccctgtt gtgactcttc gactgccac accccaatca ctgacgcgcc cgcgcgcagt     8460
tgtggcggtt actagggcgt ctcaggaatt atacatctac gacccctttg atcagcttag    8520
cgggttgttg aagttcacca aggaagcaga ggcgcaggac ttgatccacg gcccacctac    8580
agcatgccac ctgggccaag aaattgacct ttggtccaat gagggcctcg aatattacaa    8640
ggaagtcaac ctgctgtaca cacacgtccc catcaaggat ggtgtaatac acagttaccc    8700
taattgtggc cctgcctgtg gctgggaaaa gcaatccaac aaaatttcgt gcctcccgag    8760
agtggcacaa aatttgggct accactattc cccagattta ccaggatttt gccccatacc    8820
gaaagaactc gctgagcatt ggcccgtagt gtccaatgat agatacccga attgcttgca    8880
aattaccttta cagcaagtat gtgaactcag taaaccgtgc tcagcgggct atatggttgg    8940
acaatctgtt ttcgtgcaga cgcctggtgt gacatcttac tggcttactg aatgggtcga    9000
cggcaaagcg cgtgctctac cagattcctt attctcgtcc ggtaggttcg agactaacag    9060
ccgcgttttc ctcgatgaag ccgaggaaaa gtttgccgcc gctcacccct atgcctgttt    9120
```

```
gggagaaatt aataagtcca ccgtgggagg atcccacttc atcttttccc aatatttacc   9180
accactgcta cccgcaggcg ctgttgccct ggtaggtgct tcattggctg ggaaagctgc   9240
taaagctgct tgcagcgttg ttgatgtcta tgctccatcg tttgaacctt atctacaccc   9300
tgagacactg agtcgcgtgt acaagattat gatcgatttc aagccgtgta ggcttatggt   9360
gtggagaaac gcgacctttt atgtccaaga gggtgttgat gcagttacat cagcactagc   9420
agctgtgtcc aaactcatca aagtgccggc caatgagcct gtttcattcc atgtggcatc   9480
agggtacaga accaacgcgc tggtagcgcc ccaggctaaa atttcaattg agcctacgc    9540 cgccgagtgg gcactgtcaa ctgaaccgcc accggctggt tatgcgatcg tgcggcgata   9600
tattgtaaag aggctcctca gctcaacaga agtgttcttg tgccgcaggg gtgttgtgtc   9660
ttccacctca gtgcagacca tttgtgcact agagggatgt aaacctctgt tcaacttctt   9720
acaaattggt tcagtcattg ggcccgtgtg atgggcttag tgtggtcact gatttcaaat   9780
tctattcaga ctattattgc tgattttgct atttctgtga ttgatgcagc gcttttcttt   9840
ctcatgctac ttgcattggc tgttgttact gtgtttcttt tctggctcat tgttgccatc   9900
ggccgcagct tggtggcgcg tgttcacga ggtgcgcgtt acagacctgt ttaaggattt    9960
gcagtgcgac aacctgcgcg cgaaagatgc cttcccgagt ctgggacatg ctctgtcgat  10020
tggccagtcg aggctatcgt atatgctgca ggattggttg cttgctgcgc accgcaagga  10080
agttatgcct tccaatacca tgcctatgcc cggtcttact cctgattgct ttgaccatct  10140
ggagtcttct agctatgctc catttatcaa tgcctatcgg caggcaattt tgagtcaata  10200
ctcacaagag ctcctgctcg aagccatcaa ctgtaaattg cttgctgtgg ttgcaccggc  10260
attgtatcac aattaccatc tagccaattt gaccgaaccg gccacatggg tcgtgcctac  10320
agtgggccag ttgcactatt atgcttcttc ctctattttt gcttcatctg tggaagtgtt  10380
ggcagcaata atactactat ttgcatgcat accactagtg acacgagtgt acatctcttt  10440
tacgcggcta atgtcacctt cccgtcgcac ttccagcggc actttgccgc cgcgcaagat  10500
tttgtagtgc acacgggtta tgaatatgcc ggggtcacta tggtagtgca cttgtttgcc  10560
aacttggttc tgacatttcc gagcttagtt aattgttccc gccctgtgaa tgtcttttgct  10620 aatgcttctt gcgtgcaagt ggtttgtagt cataccaact caactactgg ctcgggtcaa  10680 cttttcgtttt cctttgtaga tgaagatctc cggctgcata tcaggcctac tcttatttgt  10740
tggtttgcct tgttgttggt gcactttcta cccatgccac gctacagagg ctcgcaattt  10800
tacttacact agtcatggat tgggccacgt gcacggtcat gaggggtgta ggaattttat  10860
taatgtcact cattctgcat ttcttttatct taatcccacc actctcactg cgccggctat  10920
aactcattgt ttacttctgg ttctggcagc caaaatggaa cacccaaacg ctactatctg  10980
gctgcagctg cagccgttttg ggtatcatgt ggctggcgat gtcattgtca acttggaaga  11040
gaataagagg catccttact ttaaactctt gagagcgccg gctttaccgc ttggtttgt   11100 ggctatagtt tatgttcttt tacgactggt acgttgggct caacaatgct atctatgatt  11160
gtattgttat tcttgctttg gggtgcgcca tcacatgctt acttctcata ctacaccgct  11220
cagcgcttca cagacttcac cttgtgcatg ctgacggatc gcggcgttat gccaatttg   11280 ctgcgatatg atgagcacac tgctttgtac aattgttccg ccagtaaaac ctgttggtat  11340
tgcacattcc cggacgaaaa gattatcacg tttggaaccg attgtgatga cacctacgcg  11400
gtcccagttg ctgaggtcct ggaacaggcg catggaccgt acggtgtgct gtttggtgac  11460 gtgcccccctt ttatttacta tggccgtgaa ttcggcatag ttgtgttgga tgtgtttatg  11520
```

```
ttctatcccg ttttagttct gttttctta tcagtactac cctatgctac gcttattctt    11580
gaaatgtgtg tatctattct gtttataatc tatggcattt acagcggggc ctacttggcc    11640
atgggcatat tttcggccac gcttgctata cattcaattg tggtcctccg ccaattactg    11700
tggttatgcc tggcttggcg ataccgctgc acgcttcacg cgtcctttat atcagctgag    11760
gggaaagtgt accccgtaga ccccgaactc ccggttgccg ccgcgggcaa tcggttgcta    11820
gtcccaggta ggcccactat cgattatgca gtggcctacg gcagcaaagt caaccttgtg    11880
aggttggggg cagctgaggt atgggagcca tagattcatt ttgtggtgac gggattttag    11940
gtgagtatct agattacttt attctgtccg tcccactctt gctgttgctt actaggtatg    12000
tagcatctgg gtcagtgtat gttttgactg ccttgttcta ttccttagta ttagcagctt    12060
atatttggtt tgtcatagtt ggaagagcct tttccactgc ttatgctttt gcgcttttgg    12120
ctgcttttct gttattagta acgaggatga ttgtaggtat gatgcctcgt cttcggtcca    12180
ttttcaacca tcgccaactg gtggtagctg attttgtgga cacacctagt ggacctgttc    12240
ccatcccccg ctcaactact caggtagtgg ttcgcggcaa cgggtacacc gcagttggta    12300
acaagcttgt cgatggcgtc aagacgatca cgtccgcagg ccgcctctgt tcgaaacgga    12360
tggcggcgac agcctacaag ctacaatgac ctactgcgca tgtttggtca gatgcgggtc    12420
cggaaaccgc ccgcgcaacc cactcaggct attattgcag agcctggaga ccttaggcat    12480
gatttaaatc aacaggagcg cgccacccct tcgtcgaacg tacaacggtt cttcatgatt    12540
gggcatggtt cactcactgc agatgccgga ggactcacgt acaccgtcag ttgggttcct    12600
accaaacaaa tccagcgcaa aattgcgcct ccagcagggc cgtaagacgt ggatattctc    12660
ctgtgtggcg tcatgttgaa gtagttatta gccacccagg aacc                    12704

<210> SEQ ID NO 3
<211> LENGTH: 14553
<212> TYPE: DNA
<213> ORGANISM: Equine arteritis virus

<400> SEQUENCE: 3
gctcgaagtg tgtatggtgc catatacggc tcaccgccat atgcactgca agaattacta      60
ttcttgtggg cccctctcgg taaatcctag agggctttcc tctcgttatt gcgagattcg     120
tcgttagata acggcaagtt cccttttctta ctatcctatt ttcatcttgt ggcttgacgg    180
gtcactgcca tcgtcgtcga tctctatcaa ctacccttgc gactatggca accttctccg     240
ctactggatt tggagggagt tttgttaggg actggtccct ggacttaccc gacgcttgtg     300
agcatggcgc gggattgtgc tgtgaagtgg acggctccac cttatgcgcc gagtgttttc     360
gcggttgcga aggagtggag caatgtcctg gcttgttcat gggactgtta aaactggctt     420
cgccagttcc agtgggacat aagttcctga ttggttggta tcgagctgcc aaagtcaccg     480
ggcgttacaa tttccttgag ctgttgcaac accctgcttt cgcccagctg cgtgtggttg     540
atgctaggtt agccattgaa gaggcaagtg tgtttatttc cactgaccac gcgtctgcta     600
agcgtttccc tggcgctaga tttgcgctga caccggtgta tgctaacgct tgggttgtga     660
gcccggctgc taacagtttg atagtgacca ctgaccagga acaagatggg ttctgctggt     720
taaaactttt accacctgac cgccgtgagg ctggtttgcg gttgtattac aaccattacc     780
gcgaacaaag gaccgggtgg ctgtctaaaa caggacttcg cttatggctt ggagacctgg     840
gtttgggcat caatgcgagc tctggagggc tgaaattcca cattatgagg ggttcgcctc     900
agcgagcttg gcatatcaca acacgcagct gcaagctgaa gagctactac gtttgtgaca     960
```

```
tctctgaagc agactggtcc tgtttgcccg ctggcaacta cggcggctac aatccaccag    1020
gggacggagc ttgcggttac aggtgcttgg ccttcatgaa tggcgccact gttgtgtcgg    1080
ctggttgcag ttctgacttg tggtgtgatg atgagttggc ttatcgagtc tttcaattgt    1140
cacccacgtt cacggttacc atcccaggtg ggcgagtttg tccgaatgcc aagtacgcaa    1200
tgatttgtga caagcagcac tggcgcgtca acgtgcaaa gggcgtcggc ctgtgtctcg     1260
atgaaagctg tttcaggggc acctgcaatt gccaacgcat gagtggacca ccacctgcac    1320
ccgtgtcagc cgccgtgtta gatcacatac tggaggcggc gacgtttggc aacgttcgcg    1380
tggttatacc tgaagggcag ccacgccccg taccagcgcc gcgagttcat ccctgcgcca    1440
actcttctgg agatgtcaaa gatcggcgc ccgttccgcc agtaccaaaa ccaaggacca     1500
agcttgccaa accgaaccca actcaggcgc ccatcccagc accgcgcacg cgacttcaag    1560
gggcctcaac acaggagcca ctggcgagtg cgggagttgc ttctgactcg gcacccaaat    1620
ggcgtgtggc caaaactgtg tacagctccg cggagcgctt tcggaccgaa ctggtacaac    1680
gtgctcggtc cgttggggac gttcttgttc aagcgctacc gcacaaaacc ccagcagtgc    1740
agcggtatac catgactctg aagatgatgc gttcacgctt cagttggcac tgcgacatgt    1800
ggtacccttt ggctgtaatc gcttgtttgc tccccatatg ccatctctt gctttgctcc      1860 ttagcttcgc cattgggttg atacccagtg tgggcaataa tgttgttctg acagcgcttc    1920
tggtttcatc agctaattat gttgcgtcaa tggaccatca ctgtgaaggt gcggcttgct    1980
tagccttgct ggaagaagaa cactattata gagcggtccg ttggcgcccg attacaggcg    2040
cgctgtcgct tgtgctcaat ttactggggc aggtaggcta tgtagctcgt tccaccttg     2100 atgcagctta tgttccttgc actgtgttcg atctttgcag cttttgctatt ctgtacctct   2160 gctgcaatcg ttgctggaga tgcttcggac gctgtgtgcg agttgggcct gccacgcatg    2220
ttttgggttc caccgggcaa cgagtttcca aactggcgct cattgatttg tgtgaccact    2280
tttcaaagcc caccatcgac gttgtgggca tggcaactgg ttggagcgga tgttacacag    2340
gaaccgccgc aatggagcgt cagtgtgcct ctacggtgga ccctcactcg ttcgaccaga    2400
agaaggcagg agcgattgtt tacctcaccc cccctgtcaa cagcgggtct gcgctgcagt    2460
gcctcaatgt catgtggaag cgaccaattg ggtccactgt ccttgggaa caaacaggag     2520 ctgttgtgac ggcggtcaag agcatctctt tctcacctcc ctgctgcgtc tctaccactt    2580
tgcccacccg accggtgtg accgttgtcg accatgctct ttacaaccgg ttgactgctt     2640
caggggtcga tcccgcttta ttgcgtgttg ggcaaggtga ttttctaaaa cttaatccgg    2700
ggttccggct gataggtgga tggatttatg ggatatgcta ttttgtgttg gtggttgtgt    2760
caacttttac ctgcctacct atcaaatgtg gcattggcac ccgcgaccct ttctgccgca    2820
gagtgttttc tgtacccgtc atcaagaccc aagagcactg ccatgctgga atgtgtgcta    2880
gcgctgaagg catctctctg gactctctgg ggttaactca gttacaaagt tattggatcg    2940
cagccgtcac tagcggatta tgatcttgt tggtctgcca ccgcctgcc atcagcgcct      3000 tggacttgtt gactctagct tccccttttag tgttgcttgt gttcccttgg catctgtgg    3060 ggcttttact tgcttgcagt ctcgctggtc ctgctgtgaa aatacagttg ttggcgacgc    3120 ttttttgtgaa tctgttctt ccccaagcta cccttgtcac tatgggatac tgggcgtgcg    3180
tggcggcttt ggccgtttac agtttgatgg gcttgcgagt gaaagtgaat gtgcccatgt    3240
gtgtgacacc tgcccatttt ctgctgctgg cgaggtcagc tggacagtca agagagcaga    3300
tgctccgggt cagcgctgct gcccccacca attcactgct tggagtggct cgtgattgtt    3360
```

```
atgtcacagg cacaactcgg ctgtatatac ccaaggaagg cgggatggtg tttgaagggc   3420
tattcaggtc accgaaggcg cgcggcaacg tcggcttcgt ggctggtagc agctacggca   3480
cagggtcagt gtggaccagg aacaacgagg tcgtcgtact gacagcgtca cacgtggttg   3540
gccgcgctaa catggccact ctgaagatcg gtgacgcaat gctgactctg actttcaaaa   3600
aaaatggcga cttcgccgag gcagtgacga cacagtccga gctcccaggc aattggccac   3660
agttgcattt cgcccaacca acaaccgggc ccgcttcatg gtgcactgcc acaggagatg   3720
aagaaggctt gctcagtggc gaggtttgtc tggcgtggac tactagtggc gactctggat   3780
cagcagtggt tcagggtgac gctgtggtag gggtccacac cggttcgaac acaagtggtg   3840
ttgcctacgt gaccacccca agcggaaaac tccttggcgc cgacaccgtg actttgtcgt   3900
cactgtcaaa gcatttcaca ggccctttga catcaatccc gaaggacatc cctgacaaca   3960
tcattgccga tgttgatgct gttcctcgtt ctctggccat gctgattgat ggcttatcta   4020
atagagagag cagcctttct ggacctcagt tgttgttaat tgcttgtttt atgtggtctt   4080
atcttaacca acctgcctac ttgccttatg tgctgggctt cttttgccgct aacttcttcc   4140
tgccaaaaag tgttggccgc cctgtggtca ctgggcttct atggttgtgc tgcctcttca   4200
caccgctttc catgcgcttg tgcttgttcc atctggtctg tgctaccgtc acgggaaacg   4260
tgatatcttt gtggttctac atcactgccg ctggcacgtc ttacctttct gagatgtggt   4320
tcggaggcta tcccaccttg ttgtttgtgc cacggttcct agtgtaccag ttccccggct   4380
gggctattgg cacagtacta gcggtatgca gcatcaccat gctggctgct gccctcggtc   4440
acaccctgtt actggatgtg ttctccgcct cgggtcgctt tgacaggact ttcatgatga   4500
aatacttcct ggagggagga gtgaaagaga gtgtcaccgc ctcagtcacc cgcgcttatg   4560
gcaaaccaat tacccaggag agtctcactg caacattagc tgccctcact gatgatgact   4620
tccaattcct ctctgatgtg cttgactgtc gggccgtccg atcggcaatg aatctgcgtg   4680
ccgctctcac aagttttcaa gtggcgcagt atcgtaacat ccttaatgca tccttgcaag   4740
tcgatcgtga cgctgctcgt agtcgcagac taatggcaaa actggctgat tttgcggttg   4800
aacaagaagt aacagccgga gaccgtgttg ttgttatcga cggtctggac cgcatggctc   4860
acttcaaaga cgatttggtg ctggttcctt tgaccaccaa agtagtaggc ggttctaggt   4920
gcaccatttg tgacgtcgtt aaggaagaag ccaatgacac cccagttaag ccaatgccca   4980
gcaggagacg ccgcaagggc ctgcctaaag gtgctcagtt ggagtgggac cgtcaccagg   5040
aagagaagag gaacgccggt gatgatgatt ttgcggtctc gactgattat gtcaagagag   5100
tgccaaagta ctgggatccc agcgacaccc gaggcacgac agtgaaaatc gccggcacta   5160
cctatcagaa agtggttgac tattcaggca atgtgcatta cgtggagcat caggaagatc   5220
tgctagacta cgtgctgggc aaggggagct atgaaggcct agatcaggac aaagtgttgg   5280
acctcacaaa catgcttaaa gtggacccca cggagctctc ctccaaagac aaagccaagg   5340
cgcgtcagct tgctcatctg ctgttggatc tggctaaccc agttgaggca gtgaatcagt   5400
taaactgaga gcgccccaca tctttcccgg cgatgtgggg cgtcggacat tgctgactc   5460
taaagacaag ggtttcgtgg ctctacacag tcgcacaatg ttttagctg cccgggactt   5520
tttatttaac atcaaatttg tgtgcgacga agagttcaca aagaccccaa aagacacact   5580
gcttgggtac gtacgcgcct gcccctggtta ctggtttatt ttccgtcgta cgcaccggtc   5640
actgattgat gcatactggg acagtatgga gtgcgtttac gcgcttccca ccatatctga   5700
ttttgatgtg agcccaggtg acgtcgcagt gacgggtgag cgatgggatt tgaatctcc    5760
```

```
cggaggaggc cgtgcaaaac gtctcacagc tgatctggtg cacgcttttc aagggttcca    5820
cggagcctct tattcctatg atgacaaggt ggcagctgct gtcagtggtg acccgtatcg    5880
gtcggacggc gtcttgtata acacccgttg gggcaacatt ccatattctg tcccaaccaa    5940
tgctttggaa gccacagctt gctaccgtgc tggatgtgag gccgttaccg acgggaccaa    6000
cgtcatcgca acaattgggc ccttcccgga gcaacaaccc ataccggaca tcccaaagag    6060
cgtgcttgac aactgcgctg catcagctg tgacgctttc atagcgcccg ctgcagagac    6120
agccctgtgt ggtgatttag agaaatacaa cctatccacg cagggttttg tgttgcctag    6180
tgttttctcc atggtgcggg cgtacttaaa agaggagatt ggagacgctc caccactcta    6240
cttgccatct actgtaccat ctaaaaattc acaagccgga attaacgcg ctgagttttcc    6300
tacaaggtct ttacagagct actgtttgat tgatgacatg gtgtcacagt ccatgaaaag    6360
caatctacaa accgccacca tggcgacttg taaacggcag tactgttcca aatacaagat    6420
taggagcatt ctgggcacca acaattacat tggcctaggt ttgcgtgcct gcctttcggg    6480
ggttacggcc gcattccaaa aagctggaaa ggatgggtca ccgatttatt tgggcaagtc    6540
aaaattcgac ccgatacctg ctcctgacaa gtactgcctt gaaacagacc tggagagttg    6600
tgatcgctcc accccggctt tggtgcgttg gttcgctact aatcttattt ttgagctagc    6660
tggccagccc gagttggtgc acagctacgt gttgaattgc tgtcacgatc tagttgtggc    6720
aggtagtgta gcattcacca acgcgggggg tttgtcatct ggagacccta tcacttccat    6780
ttccaatacc atctattcat tggtgctgta cacccagcac atgttgctat gtggacttga    6840
aggctatttc ccagagattg cagaaaaata tcttgatggc agcctggagc tgcgggacat    6900
gttcaagtac gttcgagtgt acatctactc ggacgatgtg gttctaacca cacccaacca    6960
gcattacgcg gccagctttg accgctgggt cccccacctg caggcgctgc taggttttcaa    7020
ggttgaccca aagaaaactg tgaacaccag ctcccctttcc tttttgggct gccggttcaa    7080
gcaagtggac ggcaagtgtt atctggccag tcttcaggac cgcgttacac gctctctgtt    7140
ataccacatt ggtgcaaaga atccctcaga gtactatgaa gctgctgttt ccatctttaa    7200
ggactccatt atctgctgtg atgaagattg gtggacggac ctccatcgac gtatcagtgg    7260
cgctgcgcgt actgacggag ttgagttccc caccattgaa atgttaacat ccttccgcac    7320
caagcagtat gagagtgccg tgtgcacagt ttgtggggcc gccccgtgg ccaagtctgc    7380
ttgtggaggg tggttctgtg gcaattgtgt cccgtaccac gtgggtcatt gtcacacaac    7440
ctcgctcttc gccaactgcg ggcacgacat catgtaccgc tccacttact gcacaatgtg    7500
tgagggttcc ccaaaacaga tggtaccaaa agtgcctcac ccgatcctgg atcatttgct    7560
gtgccacgtt gattacggca gtaaagagga actaactctg gtagtggcgg atggtcgaac    7620
aacatcaccg cccgggcgct acaaagtggg tcacaaggta gtcgccgtgg ttgcagacgt    7680
gggaggcaac attgtgtttg ggtgcggtcc tggatcacac atcgcagtac cacttcagga    7740
tacgctcaag ggcgtggtgg tgaataaagc tctgaagaac gccgccgcct ctgagtacgt    7800
ggaaggaccc cctgggagtg ggaagacttt tcacctggtc aaagatgtgc tagccgtggt    7860
cggtagcgcg accttggttg tgcccaccca cgcgtccatg ctggactgca ttaacaagct    7920
caaacaagcg ggcgccgatc catactttgt ggtgcccaag tatacagttc ttgactttcc    7980
ccggcctggc agtggaaaca tcacagtgcg actgccacag gtcggaacta gtgagggaga    8040
aacctttgtg gatgaggtgg cttacttctc accagtggat ctggcgcgca ttttaaccca    8100
gggtcgagtc aagggttacg gtgatttaaa tcagctcggg tgcgtcggac ccgcgagcgt    8160
```

```
gccacgtaac ctttggctcc gacattttgt cagcctggag cccttgcgag tgtgccatcg   8220
attcggcgct gctgtgtgtg atttgatcaa gggcatttat ccttattatg agccagctcc   8280
acataccact aaagtggtgt tgtgccaaa tccagacttt gagaaaggtg tagtcatcac    8340
cgcctaccac aaagatcgcg gtcttggtca ccgcacaatt gattcaattc aaggctgtac   8400
attccctgtt gtgactcttc gactgccac accccaatca ctgacgcgcc cgcgcgcagt    8460
tgtggcggtt actagggcgt ctcaggaatt atacatctac gaccccttg atcagcttag    8520 cgggttgttg aagttcacca aggaagcaga ggcgcaggac ttgatccacg gcccacctac   8580
agcatgccac ctgggccaag aaattgacct ttggtccaat gagggcctcg aatattacaa   8640
ggaagtcaac ctgctgtaca cacgtcccc catcaaggat ggtgtaatac acagttaccc    8700
taattgtggc cctgcctgtg ctgggaaaa gcaatccaac aaaatttcgt gcctcccgag    8760
agtggcacaa aatttgggct accactattc cccagattta ccaggatttt gccccatacc   8820
gaaagaactc gctgagcatt ggcccgtagt gtccaatgat agatacccga attgcttgca   8880
aattacctta cagcaagtat gtgaactcag taaaccgtgc tcagcgggct atatggttgg   8940
acaatctgtt ttcgtgcaga cgcctggtgt gacatcttac tggcttactg aatgggtcga   9000
cggcaaagcg cgtgctctac cagattcctt attctcgtcc ggtaggttcg agactaacag   9060
ccgcgttttc ctcgatgaag ccgaggaaaa gtttgccgcc gctcaccctc atgcctgttt   9120
gggagaaatt aataagtcca ccgtgggagg atcccactc atcttttccc aatatttacc    9180
accactgcta cccgcaggcg ctgttgccct ggtaggtgct tcattggctg ggaaagctgc   9240
taaagctgct tgcagcgttg ttgatgtcta tgctccatcg tttgaacctt atctacaccc   9300
tgagacactg agtcgcgtgt acaagattat gatcgatttc aagccgtgta ggcttatggt   9360
gtggagaaac gcgacctttt atgtccaaga gggtgttgat gcagttacat cagcactagc   9420
agctgtgtcc aaactcatca aagtgccggc caatgagcct gtttcattcc atgtggcatc   9480
agggtacaga accaacgcgc tggtagcgcc ccaggctaaa atttcaattg gagcctacgc   9540
cgccgagtgg gcactgtcaa ctgaaccgcc accggctggt tatgcgatcg tgcggcgata   9600
tattgtaaag aggctcctca gctcaacaga agtgttcttg tgccgcaggg gtgttgtgtc   9660
ttccacctca gtgcagacca tttgtgcact agagggatgt aaacctctgt tcaacttctt   9720
acaaattggt tcagtcattg ggcccgtgtg atgggcttag tgtggtcact gatttcaaat   9780
tctattcaga ctattattgc tgattttgct atttctgtga ttgatgcagc gcttttcttt   9840
ctcatgctac ttgcattggc tgttgttact gtgtttcttt tctggctcat tgttgccatc   9900
ggccgcagct tggtggcgcg tgttcacga ggtgcgcgtt acagacctgt ttaaggattt    9960
gcagtgcgac aacctgcgcg cgaaagatgc cttcccgagt ctgggacatg ctctgtcgat  10020
tggccagtcg aggctatcgt atatgctgca ggattggttg cttgctgcgc accgcaagga  10080
agttatgcct tccaatacca tgcctatgcc cggtcttact cctgattgct ttgaccatct  10140
ggagtcttct agctatgctc catttatcaa tgcctatcgg caggcaattt tgagtcaata  10200
ctcacaagag ctcctgctcg aagccatcaa ctgtaaattg cttgctgtgg ttgcaccggc  10260
attgtatcac aattaccatc tagccaattt gaccgaaccg gccacatggg tcgtgcctac  10320
agtgggccag ttgcactatt atgcttcttc ctctattttt gcttcatctg tggaagtgtt  10380
ggcagcaata atactactat ttgcatgcat accactagtg acacgagtgt acatctcttt  10440
tacgcggcta atgtcaccett cccgtcgcac ttccagcggc actttgccgc cgcgcaagat  10500
tttgtagtgc acacgggtta tgaatatgcc ggggtcacta tggtagtgca cttgtttgcc  10560
```

```
aacttggttc tgacatttcc gagcttagtt aattgttccc gccctgtgaa tgtctttgct   10620
aatgcttctt gcgtgcaagt ggtttgtagt cataccaact caactactgg ctcgggtcaa   10680
ctttcgtttt cctttgtaga tgaagatctc cggctgcata tcaggcctac tcttatttgt   10740
tggtttgcct tgttgttggt gcactttcta cccatgccac gctacagagg ctcgcaattt   10800
tacttacact agtcatggat tgggccacgt gcacggtcat gaggggtgta ggaattttat   10860
taatgtcact cattctgcat ttctttatct taatcccacc actctcactg cgccggctat   10920
aactcattgt ttacttctgg ttctggcagc caaaatggaa cacccaaacg ctactatctg   10980
gctgcagctg cagccgtttg ggtatcatgt ggctggcgat gtcattgtca acttggaaga   11040
gaataagagg catccttact ttaaactctt gagagcgccg gctttaccgc ttggttttgt   11100
ggctatagtt tatgttcttt tacgactggt acgttgggct caacaatgct atctatgatt   11160
gtattgttat tcttgctttg gggtgcgcca tcacatgctt acttctcata ctacaccgct   11220
cagcgcttca cagacttcac cttgtgcatg ctgacggatc gcggcgttat tgccaatttg   11280
ctgcgatatg atgagcacac tgcttttgtac aattgttccg ccagtaaaac ctgttggtat   11340
tgcacattcc cggacgaaaa gattatcacg tttggaaccg attgtgatga cacctacgcg   11400
gtcccagttg ctgaggtcct ggaacaggcg catggaccgt acggtgtgct gtttggtgac   11460
gtgccccctt ttatttacta tggccgtgaa ttcggcatag ttgtgttgga tgtgtttatg   11520
ttctatcccg ttttagttct gttttttctta tcagtactac cctatgctac gcttattctt   11580
gaaatgtgtg tatctattct gtttataatc tatggcattt acagcggggc ctacttggcc   11640
atgggcatat tttcggccac gcttgctata cattcaattg tggtcctccg ccaattactg   11700
tggttatgcc tggcttggcg ataccgctgc acgcttcacg cgtcctttat atcagctgag   11760
gggaaagtgt accccgtaga ccccgaactc ccggttgccg ccgcgggcaa tcggttgcta   11820
gtcccaggta ggcccactat cgattatgca gtggcctacg gcagcaaagt caaccttgtg   11880
aggttggggg cagctgaggt atgggagcca tagattcatt ttgtggtgac gggattttag   11940
gtgagtatct agattacttt attctgtccg tcccactctt gctgttgctt actaggtatg   12000
tagcatctgg gtcagtgtat gttttgactg ccttgttcta ttccttagta ttagcagctt   12060
atatttggtt tgtcatagtt ggaagagcct tttccactgc ttatgctttt gcgcttttgg   12120
ctgcttttct gttattagta acgaggatga ttgtaggtat gatgcctcgt cttcggtcca   12180
ttttcaacca tcgccaactg gtggtagctg attttgtgga cacacctagt ggacctgttc   12240
ccatcccccg ctcaactact caggtagtgg ttcgcggcaa cgggtacacc gcagttggta   12300
acaagcttgt cgatggcgtc aagacgatca cgtccgcagg ccgcctctgt tcgaaacgga   12360
tggcggcgac agcctacaag ctacaatgac ctactgcgca tgtttggtca gatgcgggtc   12420
cgcaaaccgc ccgcgcaacc cactcaggct attattgcag agcctggaga ccttaggcat   12480
gatttaaatc aacaggagcg cgccacccct tcgtcgaacg tacaacggtt cttcatgatt   12540
gggcatggtt cactcactgc agatgccgga ggactcacgt acaccgtcag ttgggttcct   12600
accaaacaaa tccagcgcaa aattgcgcct ccagcagggc cgtaagacgt ggatattctc   12660
ctgtgtggcg tcatgttgaa gtagttatta gccacccagg aaccaaaaaa aaaaaaaaa   12720 aaaactcgag gggaattaat tcttgaagac gaaagggcca ggtggcactt tcggggaaa   12780 tgtgcgcgga accctatttt gtttattttt ctaaatacat tcaaatatgt atccgctcat   12840
gagacaataa ccctgataaa tgcttcaata atattgaaaa aggaagagta tgagtattca   12900
acatttccgt gtcgccctta ttcccttttt tgcggcattt tgccttcctg tttttgctca   12960
```

-continued

```
cccagaaacg ctggtgaaag taaaagatgc tgaagatcag ttgggtgcac gagtgggtta    13020
catcgaactg gatctcaaca gcggtaagat ccttgagagt tttcgccccg aagaacgttt    13080
tccaatgatg agcacttta aagttctgct atgtggcgcg gtattatccc gtgttgacgc     13140
cgggcaagag caactcggtc gccgcataca ctattctcag aatgacttgg ttgagtactc    13200
accagtcaca gaaaagcatc ttacggatgg catgacagta agagaattat gcagtgctgc    13260
cataaccatg agtgataaca ctgcggccaa cttacttctg acaacgatcg gaggaccgaa    13320
ggagctaacc gctttttgc acaacatggg ggatcatgta actcgccttg atcgttggga     13380
accggagctg aatgaagcca taccaaacga cgagcgtgac accacgatgc ctgtagcaat    13440
ggcaacaacg ttgcgcaaac tattaactgg cgaactactt actctagctt cccggcaaca    13500
attaatagac tggatggagg cggataaagt tgcaggacca cttctgcgct cggcccttcc    13560
ggctggctgg tttattgctg ataaatctgg agccggtgag cgtgggtctc gcggtatcat    13620
tgcagcactg gggccagatg gtaagccctc ccgtatcgta gttatctaca cgacggggag    13680
tcaggcaact atggatgaac gaaatagaca gatcgctgag ataggtgcct cactgattaa    13740
gcattggtaa ctgtcagacc aagtttactc atatatactt tagattgatt taaaacttca    13800 ttttaatt aaaaggatct aggtgaagat ccttttgat aatctcatga ccaaaatccc      13860
ttaacgtgag ttttcgttcc actgagcgtc agacccgta gaaaagatca aaggatcttc     13920
ttgagatcct tttttctgc gcgtaatctg ctgcttgcaa acaaaaaac caccgctacc      13980 agcggtggtt tgtttgccgg atcaagagct accaactctt tttccgaagg taactggctt   14040
cagcagagcg cagataccaa atactgtcct tctagtgtag ccgtagttag gccaccactt    14100
caagaactct gtagcaccgc ctacatacct cgctctgcta atcctgttac cagtggctgc    14160
tgccagtggc gataagtcgt gtcttaccgg gttggactca agacgatagt taccggataa    14220
ggcgcagcgg tcgggctgaa cggggggttc gtgcacacag cccagcttgg agcgaacgac    14280
ctacaccgaa ctgagatacc tacagcgtga gctatgagaa agcgccacgc ttcccgaagg    14340
gagaaaggcg gacaggtatc cggtaagcgg cagggtcgga acaggagagc gcacgaggga    14400
gcttccaggg ggaaacgcct ggtatcttta tagtcctgtc gggtttcgcc acctctgact    14460
tgagcgtcga ttttgtgat gctcgtcagg ggggcggagc ctatggaaaa acgccagcaa    14520
cgcgagctct ctagattaat acgactcact ata                                  14553

<210> SEQ ID NO 4
<211> LENGTH: 14553
<212> TYPE: DNA
<213> ORGANISM: Equine arteritis virus

<400> SEQUENCE: 4
gctcgaagtg tgtatggtgc catatacggc tcaccgccat atgcactgca agaattacta      60
ttcttgtggg cccctctcgg taaatcctag agggctttcc tctcgttatt gcgagattcg     120
tcgttagata acggcaagtt ccctttctta ctatcctatt ttcatcttgt ggcttgacgg     180
gtcactgcca tcgtcgtcga tctctatcaa ctaccctgc gactatggca accttctccg      240
ctactggatt tggagggagt tttgttaggg actggtccct ggacttaccc gacgcttgtg     300
agcatggcgc gggattgtgc tgtgaagtgg acggctccac cttatgcgcc gagtgttttc     360
gcggttgcga aggagtggag caatgtcctg gcttgttcat gggactgtta aaactggctt     420
cgccagttcc agtgggacat aagttcctga ttggttggta tcgagctgcc aaagtcaccg     480
ggcgttacaa tttccttgag ctgttgcaac accctgcttt cgcccagctg cgtgtggttg     540
```

```
atgctaggtt agccattgaa gaggcaagtg tgtttatttc cactgaccac gcgtctgcta    600
agcgtttccc tggcgctaga tttgcgctga caccggtgta tgctaacgct tgggttgtga    660
gcccggctgc taacagtttg atagtgacca ctgaccagga acaagatggg ttctgctggt    720
taaaactttt accacctgac cgccgtgagg ctggtttgcg gttgtattac aaccattacc    780
gcgaacaaag gaccgggtgg ctgtctaaaa caggacttcg cttatggctt ggagacctgg    840
gtttgggcat caatgcgagc tctggagggc tgaaattcca cattatgagg ggttcgcctc    900
agcgagcttg gcatatcaca acacgcagct gcaagctgaa gagctactac gtttgtgaca    960
tctctgaagc agactggtcc tgtttgcccg ctggcaacta cggcggctac aatccaccag   1020
gggacggagc ttgcggttac aggtgcttgg ccttcatgaa tggcgccact gttgtgtcgg   1080
ctggttgcag ttctgacttg tggtgtgatg atgagttggc ttatcgagtc tttcaattgt   1140
cacccacgtt cacggttacc atcccaggtg ggcgagtttg tccgaatgcc aagtacgcaa   1200
tgatttgtga caagcagcac tggcgcgtca acgtgcaaa gggcgtcggc ctgtgtctcg    1260
atgaaagctg tttcagggc acctgcaatt gccaacgcat gagtggacca ccacctgcac   1320
ccgtgtcagc cgccgtgtta gatcacatac tggaggcggc gacgtttggc aacgttcgcg   1380
tggttatacc tgaagggcag ccacgccccg taccagcgcc gcgagttcat ccctgcgcca   1440
actcttctgg agatgtcaaa gatccggcgc ccgttccgcc agtaccaaaa ccaaggacca   1500
agcttgccaa accgaaccca actcaggcgc ccatcccagc accgcgcacg cgacttcaag   1560
gggcctcaac acaggagcca ctggcgagtg cgggagttgc ttctgactcg cacccaaat    1620
ggcgtgtggc caaaactgtg tacagctccg cggagcgctt tcggaccgaa ctggtacaac   1680
gtgctcggtc cgttggggac gttcttgttc aagcgctacc gcacaaaacc ccagcagtgc   1740
agcggtatac catgactctg aagatgatgc gttcacgctt cagttggcac tgcgacatgt   1800
ggtacccttt ggctgtaatc gcttgttttgc tccccatatg ccatctctt gctttgctcc    1860
ttagcttcgc cattgggttg atacccagtg tgggcaataa tgttgttctg acagcgcttc   1920
tggtttcatc agctaattat gttgcgtcaa tggaccatca ctgtgaaggt gcggcttgct   1980
tagccttgct ggaagaagaa cactattata gagcggtccg ttggcgcccg attacaggcg   2040
cgctgtcgct tgtgctcaat ttactggggc aggtaggcta tgtagctcgt tccaccttg    2100
atgcagctta tgttccttgc actgtgttcg atctttgcag cttttgctatt ctgtacctct   2160
gctgcaatcg ttgctggaga tgcttcggac gctgtgtgcg agtttgggcct gccacgcatg   2220
ttttgggttc caccgggcaa cgagtttcca aactggcgct cattgatttg tgtgaccact   2280
tttcaaagcc caccatcgac gttgtgggca tggcaactgg ttggagcgga tgttacacag   2340
gaaccgccgc aatggagcgt cagtgtgcct ctacggtgga ccctcactcg ttcgaccaga   2400
agaaggcagg agcgattgtt tacctcaccc ccctgtcaa cagcgggtct gcgctgcagt    2460
gcctcaatgt catgtggaag cgaccaattg ggtccactgt ccttgggaa caaacaggag    2520
ctgttgtgac ggcggtcaag agcatctctt tctcacctcc ctgctgcgtc tctaccactt   2580
tgcccacccg accggtgtg accgttgtcg accatgctct ttacaaccgg ttgactgctt    2640
caggggtcga tccgcttta ttgcgtgttg ggcaaggtga ttttctaaaa cttaatccgg    2700
ggttccggct gataggtgga tggatttatg ggatatgcta ttttgtgttg gtggttgtgt   2760
caacttttac ctgcctacct atcaaatgtg cattggcac ccgcgaccct ttctgccgca    2820
gagtgttttc tgtacccgtc atcaagaccc aagagcactg ccatgctgga atgtgtgcta   2880
gcgctgaagg catctctctg gactctctgg ggttaactca gttacaaagt tattggatcg   2940
```

```
cagccgtcac tagcggatta gtgatcttgt tggtctgcca ccgcctggcc atcagcgcct    3000
tggacttgtt gactctagct tcccctttag tgttgcttgt gttcccttgg gcatctgtgg    3060
ggcttttact tgcttgcagt ctcgctggtg ctgctgtgaa aatacagttg ttggcgacgc    3120
tttttgtgaa tctgttcttt ccccaagcta cccttgtcac tatgggatac tgggcgtgcg    3180
tggcggcttt ggccgtttac agtttgatgg gcttgcgagt gaaagtgaat gtgcccatgt    3240
gtgtgacacc tgcccatttt ctgctgctgg cgaggtcagc tggacagtca agagagcaga    3300
tgctccgggt cagcgctgct gcccccacca attcactgct tggagtggct cgtgattgtt    3360
atgtcacagg cacaactcgg ctgtatatac ccaaggaagg cgggatggtg tttgaagggc    3420
tattcaggtc accgaaggcg cgcggcaacg tcggcttcgt ggctggtagc agctacggca    3480
cagggtcagt gtggaccagg aacaacgagg tcgtcgtact gacagcgtca cacgtggttg    3540
gccgcgctaa catggccact ctgaagatcg gtgacgcaat gctgactctg actttcaaaa    3600
aaaatggcga cttcgccgag gcagtgacga cacagtccga gctcccaggc aattggccac    3660
agttgcattt cgcccaacca acaaccgggc ccgcttcatg gtgcactgcc acaggagatg    3720
aagaaggctt gctcagtggc gaggtttgtc tggcgtggac tactagtggc gactctggat    3780
cagcagtggt tcagggtgac gctgtggtag gggtccacac cggttcgaac acaagtggtg    3840
ttgcctacgt gaccaccccca gcggaaaaac tccttggcgc cgacaccgtg actttgtcgt    3900
cactgtcaaa gcatttcaca ggccctttga catcaatccc gaaggacatc cctgacaaca    3960
tcattgccga tgttgatgct gttcctcgtt ctctggccat gctgattgat ggcttatcta    4020
atagagagag cagcctttct ggacctcagt tgttgttaat tgcttgtttt atgtggtctt    4080
atcttaacca acctgcctac ttgccttatg tgctgggctt ctttgccgct aacttcttcc    4140
tgccaaaaag tgttggccgc cctgtggtca ctgggcttct atggttgtgc tgcctcttca    4200
caccgctttc catgcgcttg tgcttgttcc atctggtctg tgctaccgtc acgggaaacg    4260
tgatatcttt gtggttctac atcactgccg ctggcacgtc ttacctttct gagatgtggt    4320
tcggaggcta tcccaccttg ttgtttgtgc cacggttcct agtgtaccag ttccccggct    4380
gggctattgg cacagtacta gcggtatgca gcatcaccat gctggctgct gccctcggtc    4440
acaccctgtt actggatgtg ttctccgcct cgggtcgctt tgacaggact ttcatgatga    4500
aatacttcct ggagggagga gtgaaagaga gtgtcaccgc ctcagtcacc cgcgcttatg    4560
gcaaaccaat tacccaggag agtctcactg caacattagc tgccctcact gatgatgact    4620
tccaattcct ctctgatgtg cttgactgtc gggccgtccg atcggcaatg aatctgcgtg    4680
ccgctctcac aagttttcaa gtggcgcagt atcgtaacat ccttaatgca tccttgcaag    4740
tcgatcgtga cgctgctcgt agtcgcagac taatggcaaa actggctgat tttgcggttg    4800
aacaagaagt aacagccgga gaccgtgttg ttgttatcga cggtctggac cgcatggctc    4860
acttcaaaga cgatttggtg ctggttcctt tgaccaccaa agtagtaggc ggttctaggt    4920
gcaccatttg tgacgtcgtt aaggaagaag ccaatgacac cccagttaag ccaatgccca    4980
gcaggagacg ccgcaagggc ctgcctaaag gtgctcagtt ggagtgggac cgtcaccagg    5040
aagagaagag gaacgccggt gatgatgatt ttgcggtctc gactgattat gtcaagagag    5100
tgccaaagta ctgggatccc agcgacaccc gaggcacgac agtgaaaatc gccggcacta    5160
cctatcagaa agtggttgac tattcaggca atgtgcatta cgtggagcat caggaagatc    5220
tgctagacta cgtgctgggc aaggggagct atgaaggcct agatcaggac aaagtgttgg    5280
acctcacaaa catgcttaaa gtggaccccca cggagctctc ctccaaagac aaagccaagg    5340
```

```
cgcgtcagct tgctcatctg ctgttggatc tggctaaccc agttgaggca gtgaatcagt    5400
taaactgaga gcgccccaca tctttcccgg cgatgtgggg cgtcggacat ttgctgactc    5460
taaagacaag ggtttcgtgg ctctacacag tcgcacaatg tttttagctg cccgggactt    5520
tttatttaac atcaaatttg tgtgcgacga agagttcaca aagaccccaa aagacacact    5580
gcttgggtac gtacgcgcct gccctggtta ctggtttatt ttccgtcgta cgcaccggtc    5640
actgattgat gcatactggg acagtatgga gtgcgtttac gcgcttccca ccatatctga    5700
ttttgatgtg agcccaggtg acgtcgcagt gacgggtgag cgatgggatt ttgaatctcc    5760
cggaggaggc cgtgcaaaac gtctcacagc tgatctggtg cacgcttttc aagggttcca    5820
cggagcctct tattcctatg atgacaaggt ggcagctgct gtcagtggtg acccgtatcg    5880
gtcggacggc gtcttgtata cacccgttg gggcaacatt ccatattctg tcccaaccaa    5940
tgctttggaa gccacagctt gctaccgtgc tggatgtgag gccgttaccg acgggaccaa    6000
cgtcatcgca acaattgggc ccttcccgga gcaacaaccc ataccggaca tcccaaagag    6060
cgtgcttgac aactgcgctg acatcagctg tgacgctttc atagcgcccg ctgcagagac    6120
agccctgtgt ggtgatttag agaaatacaa cctatccacg cagggttttg tgttgcctag    6180
tgttttctcc atggtgcggg cgtacttaaa agaggagatt ggagacgctc caccactcta    6240
cttgccatct actgtaccat ctaaaaattc acaagccgga attaacgcg ctgagtttcc    6300 tacaaggtct ttacagagct actgtttgat tgatgacatg gtgtcacagt ccatgaaaag    6360
caatctacaa accgccacca tggcgacttg taaacggcag tactgttcca aatacaagat    6420
taggagcatt ctgggcacca acaattacat tggcctaggt ttgcgtgcct gcctttcggg    6480
ggttacggcc gcattccaaa aagctggaaa ggatgggtca ccgatttatt tgggcaagtc    6540
aaaattcgac ccgatacctg ctcctgacaa gtactgcctt gaaacagacc tggagagttg    6600
tgatcgctcc accccggctt tggtgcgttg gttcgctact aatcttattt ttgagctagc    6660
tggccagccc gagttggtgc acagctacgt gttgaattgc tgtcacgatc tagttgtggc    6720
aggtagtgta gcattcacca aacgcggggg tttgtcatct ggagaccta tcacttccat    6780 ttccaatacc atctattcat tggtgctgta cacccagcac atgttgctat gtggacttga    6840
aggctatttc ccagagattg cagaaaaata tcttgatggc agcctggagc tgcgggacat    6900
gttcaagtac gttcgagtgt acatctactc ggacgatgtg gttctaacca cacccaacca    6960
gcattacgcg gccagctttg accgctgggt cccccacctg caggcgctgc taggtttcaa    7020
ggttgaccca aagaaaactg tgaacaccag ctccccttcc tttttgggct gccggttcaa    7080
gcaagtggac ggcaagtgtt atctggccag tcttcaggac cgcgttacac gctctctgtt    7140
ataccacatt ggtgcaaaga atccctcaga gtactatgaa gctgctgttt ccatctttaa    7200
ggactccatt atctgctgtg atgaagattg gtggacggac ctccatcgac gtatcagtgg    7260
cgctgcgcgt actgacggag ttgagttccc caccattgaa atgttaacat ccttccgcac    7320
caagcagtat gagagtgccg tgtgcacagt ttgtgggggcc gccccgtgg ccaagtctgc    7380 ttgtggaggg tggttctgtg gcaattgtgt cccgtaccac gtgggtcatt gtcacacaac    7440
ctcgctcttc gccaactgcg ggcacgacat catgtaccgc tccacttact gcacaatgtg    7500
tgagggttcc ccaaaacaga tggtaccaaa agtgcctcac ccgatcctgg atcatttgct    7560
gtgccacgtt gattacggca gtaaagagga actaactctg gtagtggcgg atggtcgaac    7620
aacatcaccg cccgggcgct acaaagtggg tcacaaggta gtcgccgtgg ttgcagacgt    7680
gggaggcaac attgtgtttg ggtgcggtcc tggatcacac atcgcagtac cacttcagga    7740
```

```
tacgctcaag ggcgtggtgg tgaataaagc tctgaagaac gccgccgcct ctgagtacgt    7800
ggaaggaccc cctgggagtg ggaagacttt tcacctggtc aaagatgtgc tagccgtggt    7860
cggtagcgcg accttggttg tgcccaccca cgcgtccatg ctggactgca ttaacaagct    7920
caaacaagcg ggcgccgatc catactttgt ggtgcccaag tatacagttc ttgactttcc    7980
ccggcctggc agtggaaaca tcacagtgcg actgccacag gtcggaacta gtgagggaga    8040
aacctttgtg gatgaggtgg cttacttctc accagtggat ctggcgcgca ttttaaccca    8100
gggtcgagtc aagggttacg gtgatttaaa tcagctcggg tgcgtcggac ccgcgagcgt    8160
gccacgtaac cttggctcc gacattttgt cagcctggag cccttgcgag tgtgccatcg    8220
attcggcgct gctgtgtgtg atttgatcaa gggcatttat ccttattatg agccagctcc    8280
acataccact aaagtggtgt tgtgccaaa tccagacttt gagaaaggtg tagtcatcac    8340
cgcctaccac aaagatcgcg gtcttggtca ccgcacaatt gattcaattc aaggctgtac    8400
attccctgtt gtgactcttc gactgccac accccaatca ctgacgcgcc cgcgcgcagt    8460
tgtggcggtt actagggcgt ctcaggaatt atacatctac gaccccttgg atcagcttag    8520
cgggttgttg aagttcacca aggaagcaga ggcgcaggac ttgatccacg cccacctac    8580 agcatgccac ctgggccaag aaattgacct ttggtccaat gagggcctcg aatattacaa    8640
ggaagtcaac ctgctgtaca cacgtcccc catcaaggat ggtgtaatac acagttaccc    8700
taattgtggc cctgcctgtg gctgggaaaa gcaatccaac aaaatttcgt gcctcccgag    8760
agtggcacaa aatttgggct accactattc cccagattta ccaggatttt gccccatacc    8820
gaaagaactc gctgagcatt ggcccgtagt gtccaatgat agatacccga attgcttgca    8880 aattaccta cagcaagtat gtgaactcag taaaccgtgc tcagcgggct atatggttgg    8940
acaatctgtt ttcgtgcaga cgcctggtgt gacatcttac tggcttactg aatgggtcga    9000
cggcaaagcg cgtgctctac cagattcctt attctcgtcc ggtaggttcg agactaacag    9060
ccgcgttttc ctcgatgaag ccgaggaaaa gtttgccgcc gctcacctc atgcctgttt    9120 gggagaaatt aataagtcca ccgtgggagg atcccactc atcttttccc aatatttacc    9180
accactgcta cccgcaggcg ctgttgccct ggtaggtgct tcattggctg ggaaagctgc    9240
taaagctgct tgcagcgttg ttgatgtcta tgctccatcg tttgaacctt atctacaccc    9300
tgagacactg agtcgcgtgt acaagattat gatcgatttc aagccgtgta ggcttatggt    9360
gtggagaaac gcgaccttt atgtccaaga gggtgttgat gcagttacat cagcactagc    9420
agctgtgtcc aaactcatca aagtgccggc caatgagcct gtttcattcc atgtggcatc    9480
agggtacaga accaacgcgc tggtagcgcc ccaggctaaa atttcaattg gagcctacgc    9540
cgccgagtgg gcactgtcaa ctgaaccgcc accggctggt tatgcgatcg tgcggcgata    9600
tattgtaaag aggctcctca gctcaacaga gtgttcttg tgccgcaggg gtgttgtgtc    9660
ttccacctca gtgcagacca tttgtgcact agagggatgt aaacctctgt tcaacttctt    9720
acaaattggt tcagtcattg ggcccgtgtg atgggcttag tgtggtcact gatttcaaat    9780
tctattcaga ctattattgc tgattttgct atttctgtga ttgatgcagc gcttttcttt    9840
ctcatgctac ttgcattggc tgttgttact gtgtttcttt tctggctcat tgttgccatc    9900
ggccgcagct tggtggcgcg tgttcacga ggtgcgcgtt acagacctgt ttaaggattt    9960
gcagtgcgac aacctgcgcg cgaaagatgc cttcccgagt ctgggacatg ctctgtcgat   10020
tggccagtcg aggctatcgt atatgctgca ggattggttg cttgctgcgc accgcaagga   10080
agttatgcct tccaatacca tgcctatgcc cggtcttact cctgattgct ttgaccatct   10140
```

```
ggagtcttct agctatgctc catttatcaa tgcctatcgg caggcaattt tgagtcaata   10200
ctcacaagag ctcctgctcg aagccatcaa ctgtaaattg cttgctgtgg ttgcaccggc   10260
attgtatcac aattaccatc tagccaattt gaccgaaccg ccacatggg tcgtgcctac    10320
agtgggccag ttgcactatt atgcttcttc ctctattttt gcttcatctg tggaagtgtt   10380
ggcagcaata atactactat ttgcatgcat accactagtg acacgagtgt acatctcttt   10440
tacgcggcta atgtcacctt cccgtcgcac ttccagcggc actttgccgc cgcgcaagat   10500
tttgtagtgc acacgggtta tgaatatgcc ggggtcacta tggtagtgca cttgtttgcc   10560
aacttggttc tgacatttcc gagcttagtt aattgttccc gccctgtgaa tgtctttgct   10620
aatgcttctt gcgtgcaagt ggtttgtagt cataccaact caactactgg ctcgggtcaa   10680
ctttcgtttt cctttgtaga tgaagatctc cggctgcata tcaggcctac tcttatttgt   10740
tggtttgcct tgttgttggt gcactttcta cccatgccac gctacagagg ctcgcaattt   10800
tacttacact agtcatggat tgggccacgt gcacggtcat gaggggtgta ggaattttat   10860
taatgtcact cattctgcat ttctttatct taatcccacc actctcactg cgccggctat   10920
aactcattgt ttacttctgg ttctggcagc caaaatggaa cacccaaacg ctactatctg   10980
gctgcagctg cagccgtttg ggtatcatgt ggctggcgat gtcattgtca acttggaaga   11040
gaataagagg catccttact ttaaactctt gagagcgccg gctttaccgc ttggttttgt   11100
ggctatagtt tatgttcttt tacgactggt acgttgggct caacaatgct atctatgatt   11160
gtattgttat tcttgctttg gggtgcgcca tcacatgctt acttctcata ctacaccgct   11220
cagcgcttca cagacttcac cttgtgcatg ctgacggatc gcggcgttat tgccaatttg   11280
ctgcgatatg atgagcacac tgctttgtac aattgttccg ccagtaaaac ctgttggtat   11340
tgcacattcc cggacgaaaa gattatcacg tttggaaccg attgtgatga cacctacgcg   11400
gtcccagttg ctgaggtcct ggaacaggcg catggaccgt acggtgtgct gtttggtgac   11460
gtgccccctt ttatttacta tggccgtgaa ttcggcatag ttgtgttgga tgtgtttatg   11520
ttctatcccg ttttagttct gtttttctta tcagtactac cctatgctac gcttattctt   11580
gaaatgtgtg tatctattct gtttataatc tatggcattt acagcggggc ctacttggcc   11640
atgggcatat tttcggccac gcttgctata cattcaattg tggtcctccg ccaattactg   11700
tggttatgcc tggcttggcg ataccgctgc acgcttcacg cgtcctttat atcagctgag   11760
gggaaagtgt accccgtaga ccccgaactc ccggttgccg ccgcgggcaa tcggttgcta   11820
gtcccaggta ggcccactat cgattatgca gtggcctacg gcagcaaagt caaccttgtg   11880
aggttggggg cagctgaggt atgggagcca tagattcatt ttgtggtgac gggattttag   11940
gtgagtatct agattacttt attctgtccg tcccactctt gctgttgctt actaggtatg   12000
tagcatctgg gtcagtgtat gttttgactg ccttgttcta ttccttagta ttagcagctt   12060
atatttggtt tgtcatagtt ggaagagcct tttccactgc ttatgctttt gcgcttttgg   12120
ctgcttttct gttattagta acgaggatga ttgtaggtat gatgcctcgt cttcggtcca   12180
ttttcaacca tcgccaactg gtggtagctg attttgtgga cacacctagt ggacctgttc   12240
ccatcccccg ctcaactact caggtagtgg ttcgcggcaa cgggtacacc gcagttggta   12300
acaagcttgt cgatggcgtc aagacgatca cgtccgcagg ccgcctctgt tcgaaacgga   12360
tggcggcgac agcctacaag ctacaatgac ctactcgcga tgtttggtca gatgcgggtc   12420
cggaaaccgc ccgcgcaacc cactcaggct attattgcag agcctggaga ccttaggcat   12480
gatttaaatc aacaggagcg cgccaccctt tcgtcgaacg tacaacggtt cttcatgatt   12540
```

```
gggcatggtt cactcactgc agatgccgga ggactcacgt acaccgtcag ttgggttcct    12600
accaaacaaa tccagcgcaa aattgcgcct ccagcagggc cgtaagacgt ggatattctc    12660
ctgtgtggcg tcatgttgaa gtagttatta gccacccagg aaccaaaaaa aaaaaaaaaa    12720
aaaactcgag gggaattaat tcttgaagac gaaagggcca ggtggcactt ttcggggaaa    12780
tgtgcgcgga acccctattt gtttattttt ctaaatacat tcaaatatgt atccgctcat    12840
gagacaataa ccctgataaa tgcttcaata atattgaaaa aggaagagta tgagtattca    12900
acatttccgt gtcgccctta ttcccttttt tgcggcattt tgccttcctg ttttgctca     12960
cccagaaacg ctggtgaaag taaaagatgc tgaagatcag ttgggtgcac gagtgggtta    13020
catcgaactg gatctcaaca gcggtaagat ccttgagagt tttcgccccg aagaacgttt    13080
tccaatgatg agcactttta aagttctgct atgtggcgcg gtattatccc gtgttgacgc    13140
cgggcaagag caactcggtc gccgcataca ctattctcag aatgacttgg ttgagtactc    13200
accagtcaca gaaaagcatc ttacggatgg catgacagta agagaattat gcagtgctgc    13260
cataaccatg agtgataaca ctgcggccaa cttacttctg acaacgatcg gaggaccgaa    13320
ggagctaacc gcttttttgc acaacatggg ggatcatgta actcgccttg atcgttggga    13380
accggagctg aatgaagcca taccaaacga cgagcgtgac accacgatgc ctgtagcaat    13440
ggcaacaacg ttgcgcaaac tattaactgg cgaactactt actctagctt cccggcaaca    13500
attaatagac tggatggagg cggataaagt tgcaggacca cttctgcgct cggcccttcc    13560
ggctggctgg tttattgctg ataaatctgg agccggtgag cgtgggtctc gcggtatcat    13620
tgcagcactg gggccagatg gtaagccctc ccgtatcgta gttatctaca cgacggggag    13680
tcaggcaact atggatgaac gaaatagaca gatcgctgag ataggtgcct cactgattaa    13740
gcattggtaa ctgtcagacc aagtttactc atatatactt tagattgatt taaaacttca    13800
tttttaattt aaaaggatct aggtgaagat cctttttgat aatctcatga ccaaaatccc    13860
ttaacgtgag ttttcgttcc actgagcgtc agaccccgta gaaaagatca aggatcttc     13920
ttgagatcct ttttttctgc gcgtaatctg ctgcttgcaa acaaaaaaac caccgctacc    13980
agcggtggtt tgtttgccgg atcaagagct accaactctt tttccgaagg taactggctt    14040
cagcagagcg cagataccaa atactgtcct tctagtgtag ccgtagttag gccaccactt    14100
caagaactct gtagcaccgc ctacatacct cgctctgcta atcctgttac cagtggctgc    14160
tgccagtggc gataagtcgt gtcttaccgg gttggactca agacgatagt taccggataa    14220
ggcgcagcgg tcgggctgaa cggggggttc gtgcacacag cccagcttgg agcgaacgac    14280
ctacaccgaa ctgagatacc tacagcgtga gctatgagaa agcgccacgc ttcccgaagg    14340
gagaaaggcg gacaggtatc cggtaagcgg cagggtcgga acaggagagc gcacgaggga    14400
gcttccaggg ggaaacgcct ggtatcttta tagtcctgtc gggtttcgcc acctctgact    14460
tgagcgtcga ttttgtgat gctcgtcagg ggggcggagc ctatgaaaa acgccagcaa      14520
cgcgagctct ctagattaat acgactcact ata                                14553
```

<210> SEQ ID NO 5
<211> LENGTH: 20
<212> TYPE: DNA
<213> ORGANISM: Artificial Sequence
<220> FEATURE:
<223> OTHER INFORMATION: Primers for RT-PCR amplification of EAV MLV

<400> SEQUENCE: 5
gtcatcatca gtgagggcag                                                  20

<210> SEQ ID NO 6
<211> LENGTH: 55
<212> TYPE: DNA
<213> ORGANISM: Artificial sequence
<220> FEATURE:
<223> OTHER INFORMATION: Primer for RT-PCR amplification of EAV MLV

<400> SEQUENCE: 6
caacgcgagc tctctagatt aatacgactc actatagctc gaagtgtgta tggtg         55

<210> SEQ ID NO 7
<211> LENGTH: 29
<212> TYPE: DNA
<213> ORGANISM: Artificial sequence
<220> FEATURE:
<223> OTHER INFORMATION: Primer for RT-PCR amplification of EAV MLV

<400> SEQUENCE: 7
ggtaagacgt gccagcggca gtgatgtag                                       29

<210> SEQ ID NO 8
<211> LENGTH: 20
<212> TYPE: DNA
<213> ORGANISM: Artificial Sequence
<220> FEATURE:
<223> OTHER INFORMATION: Primers for RT-PCR amplification of EAV MLV

<400> SEQUENCE: 8
cccccgcgtt tggtgaatgc                                                 20

<210> SEQ ID NO 9
<211> LENGTH: 20
<212> TYPE: DNA
<213> ORGANISM: Artificial sequence
<220> FEATURE:
<223> OTHER INFORMATION: primers for RT-PCR amplification of EAV MLV

<400> SEQUENCE: 9
tgcttgttcc atctggtctg                                                 20

<210> SEQ ID NO 10
<211> LENGTH: 20
<212> TYPE: DNA
<213> ORGANISM: Artificial sequence
<220> FEATURE:
<223> OTHER INFORMATION: primers for RT-PCR amplification of EAV MLV

<400> SEQUENCE: 10
tctccaggtc tgtttcaagg                                                 20

<210> SEQ ID NO 11
<211> LENGTH: 20
<212> TYPE: DNA
<213> ORGANISM: Artificial sequence
<220> FEATURE:
<223> OTHER INFORMATION: primers for RT-PCR amplification of EAV MLV

<400> SEQUENCE: 11
acttctgttg agctgaggag                                                 20

<210> SEQ ID NO 12
<211> LENGTH: 21
<212> TYPE: DNA
<213> ORGANISM: Artificial sequence
<220> FEATURE:
<223> OTHER INFORMATION: primers for RT-PCR amplification of EAV MLV

```
<400> SEQUENCE: 12
attaggagca ttctgggcac c                                              21

<210> SEQ ID NO 13
<211> LENGTH: 20
<212> TYPE: DNA
<213> ORGANISM: Artificial sequence
<220> FEATURE:
<223> OTHER INFORMATION: primers for RT-PCR amplification of EAV MLV

<400> SEQUENCE: 13
acgcgactca gtgtctcagg                                                20

<210> SEQ ID NO 14
<211> LENGTH: 67
<212> TYPE: DNA
<213> ORGANISM: Artificial sequence
<220> FEATURE:
<223> OTHER INFORMATION: primers for RT-PCR amplification of EAV MLV

<400> SEQUENCE: 14
gcactcagct agtagacatc ctcgagtttt ttttttttt tttttggtt cctgggtggc      60 taataac                                                              67

<210> SEQ ID NO 15
<211> LENGTH: 21
<212> TYPE: DNA
<213> ORGANISM: Artificial sequence
<220> FEATURE:
<223> OTHER INFORMATION: primers for RT-PCR amplification of EAV MLV

<400> SEQUENCE: 15
tattctcgtc cggtaggttc g                                              21

<210> SEQ ID NO 16
<211> LENGTH: 24
<212> TYPE: DNA
<213> ORGANISM: Artificial sequence
<220> FEATURE:
<223> OTHER INFORMATION: primers for RT-PCR amplification of EAV MLV

<400> SEQUENCE: 16
gcactcagct agtagacatc ctcg                                           24

<210> SEQ ID NO 17
<211> LENGTH: 25
<212> TYPE: DNA
<213> ORGANISM: Artificial sequence
<220> FEATURE:
<223> OTHER INFORMATION: mutagenesis primer

<400> SEQUENCE: 17
gatgcgggtc cggaaaccgc ccgcg                                          25

<210> SEQ ID NO 18
<211> LENGTH: 25
<212> TYPE: DNA
<213> ORGANISM: Artificial sequence
<220> FEATURE:
<223> OTHER INFORMATION: mutagenesis primer

<400> SEQUENCE: 18
cgcgggcggt ttccggaccc gcatc                                          25
```

INFECTIOUS CDNA CLONE OF THE MODIFIED LIVE VIRUS VACCINE STRAIN OF *EQUINE ARTERITIS* VIRUS

This utility patent application claims the benefit of priority in U.S. Provisional Patent Application Ser. No. 61/156,595 filed on Mar. 2, 2009, the entirety of the disclosure of which is incorporated herein by reference.

TECHNICAL FIELD

The present invention relates to an infectious clone of the modified live virus (MLV) vaccine strain of Equine arteritis Virus (EAV). In particular, the invention relates to an infectious cDNA clone of the MLV vaccine strain allowing generation of full length, infectious transcripts of MLV EAV. Use of the functional, infectious recombinant virion of EAV derived from an attenuated vaccine strain in marker vaccines, companion diagnostic tests, and the like is contemplated.

BACKGROUND OF THE INVENTION

Equine arteritis virus (EAV) is a member of the genus *Arterivirus*, family Arteriviridae in the order Nidovirales (Cavanagh, 1997), and is the causative agent of equine viral arteritis (EVA) of horses (Doll et al., 1957a). Outbreaks of EVA are characterized by any combination of systemic illness of adult horses, abortion of pregnant mares, interstitial pneumonia of young foals and persistent infection of stallions (Doll et al., 1957a; Doll et al., 1957b; Golnik et al., 1981; Timoney et al. 1986; Timoney et al., 1987; Timoncy et al., 1992; Carman et al., 1988; Vaala et al., 1992; Del Piero et al., 1995; Del Piero et al., 1997). EAV is horizontally transmitted either by aerosol during outbreaks of EVA or venerally via the breeding of an infected stallion to susceptible mares, and vertically through congenital infection of foals born to mares infected late in gestation (Timoney et al., 1987; Timoney et al., 1992; Vaala et al., 1992; Timoney and McCollum, 1993; Glaser et al., 1996).

Dissemination of EAV by fomites such as vehicles, twitches, artificial vaginas and shanks can be an important source of infection in some outbreaks (Collins et al. 1987; Timoney and McCollum, 1988; Timoney and McCollum, 1993). The persistently infected carrier stallion clearly plays an important role in perpetuation and sexual dissemination of EAV. The persistence of EAV in the male reproductive tract is testosterone-dependent (Timoney and McCollum, 1993). It was recently shown that EAV behaves as a quasi-species during persistent infection of carrier stallions, with regular emergence of novel genotypic and phenotypic viral variants (Hedges et al., 1999).

The EAV genome is 12.7 kb and contains 5' and 3' untranslated regions and nine functional open reading frames [ORFs; (Snijder and Meulenberg, 1998. Snijder et al., 1999)]. ORFs 1a and 1b encode two replicase polyproteins [pp1a and pp1ab; (de Vries et al., 1997; Snijder and Spaan, 2006; Snijder and Meulenberg, 1998)], and the remaining seven ORFs (2a, 2b and 3-7) encode structural proteins of the virus. These include four membrane glycoproteins GP2 (25 kDa), GP3 (3642 kDa), GP4 (28 kDa) and GP5 (30-44 kDa), respectively encoded by ORFs 2b, 3, 4, and 5, two unglycosylated membrane proteins E (8 kDa) and M (17 kDa) encoded by ORFs 2a and 6, and the phosphorylated nucleocapsid protein N (14 kDa) encoded by ORF7 (de Vries et al., 1992; Snijder et al., 1999; Wieringa et al, 2002).

Prevention and control of EVA in North America is achieved by vaccination of horses with the modified live virus vaccine strain of EAV (ARVAC®, Fort Dodge Animal Health; Moore, 1986). Although the current modified live virus (MLV) vaccine against EVA is safe and efficacious, there is resistance to using it in horses in many countries (e.g. European Union) regardless of the seroprevalence of EAV infection. One of the major concerns is the safety of the current MLV vaccine in pregnant mares, in particular the ability of the attenuated virus to cross the placenta and infects the unborn foal. The vaccine is only recommended for use in stallions and nonpregnant mares. It is not recommended for use in pregnant mares, especially during the last two months of gestation, or in foals less than 6 weeks of age, unless they are at high risk of natural exposure. Furthermore, horses that are vaccinated with the current MLV cannot be distinguished from naturally infected animals. Following the recent multistate EVA occurrence in the United States there is a strong industry demand for a marker vaccine to distinguish vaccinated animals from the naturally infected animals, as well as to develop a MLV vaccine that is totally safe for use in pregnant mares. Thus, there remains a need in the art for novel means for control of outbreaks of EAV. The advent of recombinant DNA technology has helped to develop new generation vaccines against a number of veterinary pathogens. These include live-vectored vaccines, gene deletion mutants and DNA vaccines.

SUMMARY OF THE INVENTION

To solve the aforementioned problems, there is provided an isolated polynucleotide molecule comprising a DNA sequence which encodes an infectious RNA molecule encoding a modified live virus vaccine strain of an Equine arteritis virus. That polynucleotide sequence is derived from an Equine arteritis virus modified live virus vaccine strain (ARVAC®, Fort Dodge Animal Health). In one embodiment, the polynucleotide sequence is SEQ ID NO:1 or a degenerate variant thereof. Vectors, including plasmid vectors, comprising the polynucleotide molecule are provided. Still further, an isolated infectious RNA molecule encoded by the isolated polynucleotide molecule is provided, which encodes a modified live virus vaccine strain of the Equine arteritis virus.

In another aspect, there is provided an isolated polynucleotide molecule comprising a DNA sequence which encodes an infectious RNA molecule encoding an Equine arteritis virus, wherein the DNA sequence is SEQ TD NO:2 or a degenerate variant thereof. In this embodiment, a silent point mutation is introduced, allowing recognition and distinguishing the sequence from the parent strain Equine arteritis virus or other strains of the virus. Vectors, host cells transfected with the polynucleotide molecule, and infectious RNA molecules encoded by the polynucleotide molecule are provided also.

These and other embodiments, aspects, advantages, and features of the present invention will be set forth in the description which follows, and in part will become apparent to those of ordinary skill in the art by reference to the following description of the invention and referenced drawings or by practice of the invention. The aspects, advantages, and features of the invention are realized and attained by means of the instrumentalities, procedures, and combinations particularly pointed out in the appended claims. Various patent and non-patent citations are discussed herein. Unless otherwise indicated, any such citations are specifically incorporated by reference in their entirety into the present disclosure.

BRIEF DESCRIPTION OF THE DRAWINGS

The accompanying drawings incorporated in and forming a part of the specification, illustrate several aspects of the present invention, and together with the description serve to explain the principles of the invention. In the drawings.

DETAILED DESCRIPTION OF THE ILLUSTRATED EMBODIMENTS

In the following detailed description of the illustrated embodiments, reference is made to the accompanying drawings that form a part hereof, and in which is shown by way of illustration, specific embodiments in which the invention may be practiced. These embodiments are described in sufficient detail to enable those skilled in the art to practice the invention. Also, it is to be understood that other embodiments may be utilized and that process, reagent, software, and/or other changes may be made without departing from the scope of the present invention.

EXAMPLE 1

Figure 1:
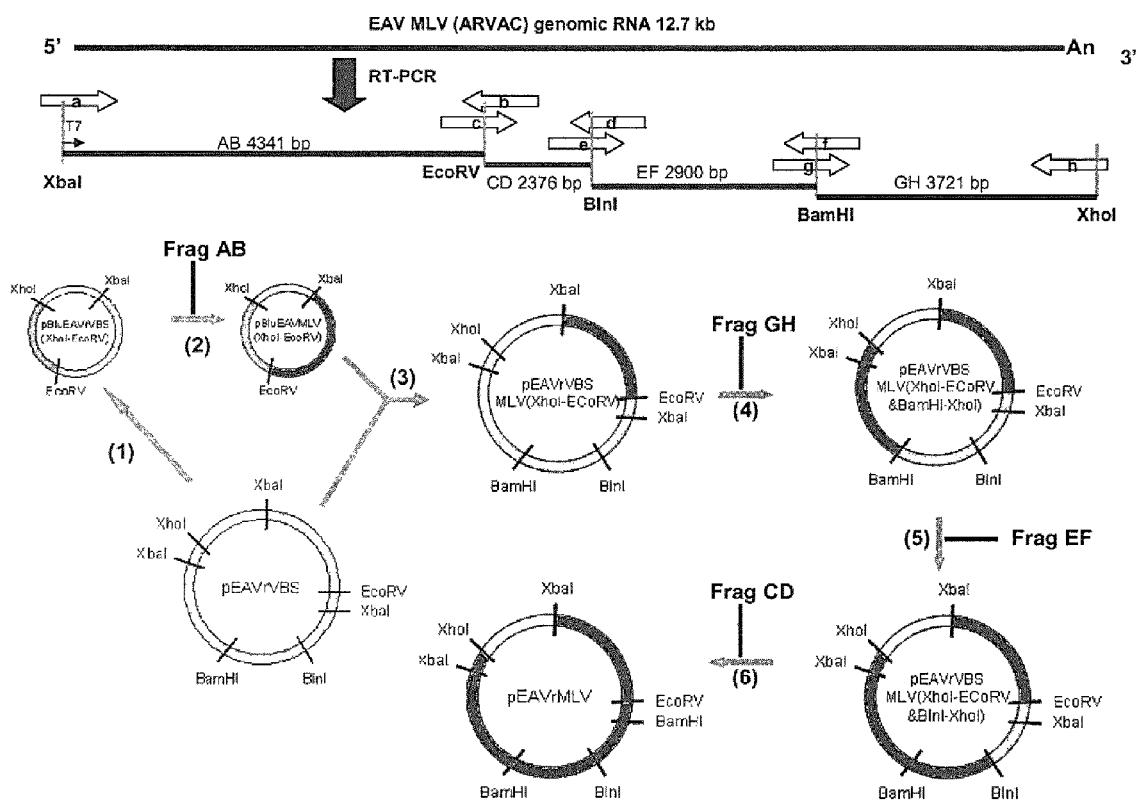
FIG. 1 presents a schematic in flow diagram form of a cloning strategy for constructing a full-length infectious cDNA clone of the Equine arteritis virus modified live vaccine strain (ARVAC®)

FIG. 1 shows in flow diagram the strategy employed for construction of a full-length infectious cDNA clone of EAV MLV. The experimental details for this strategy have been previously set forth (Balasuriya et al., 2007; incorporated herein by reference). Briefly, the pTRSB plasmid sequence (McKnight et al., 1996) used in making in the virulent pEAVrVBS infectious cDNA clone (Balasuriya et al., 2007; GenBank accession no. DQ846751) was used as the backbone to construct the EAV MLV clone.

The viral RNA of EAV MLV strain (ARVAC®, Fort Dodge Animal Health) was RT-PCR amplified using four pairs of synthetic oligonucleotide primers (a & b, c & d, e & f, and g & h), designed according to the EAV MLV nucleotide sequence (GenBank accession no. EU586275) to obtain four overlapping fragments (termed AB, CD, EF, and GH). Long PCR was carried out according to the manufacturers instructions with the Expand Long Template PCR system (Boehringer Mannheim). The primers used are set forth in Table 1.

With reference to FIG. 1, in step 1 a shuttle vector pBluEAVrVBS(XhoI-EcoRV) was constructed by replacing the fragment XhoI-EcoRV of the plasmid pBlu2SKP with the fragment XhoI-EcoRV of the full-length clone pEAVrVBS. Next (step 2), the fragment AB was digested with restriction enzymes XbaI and EcoRV and then cloned into the shuttle vector pBluEAVrVBS(XhoI-EcoRV) which was also cut with the same restriction enzymes, to obtain the recombinant plasmid pBluEAVMLV(XhoI-EcoRV). In step 3, the plasmid pBluEAVMLV(XhoI-EcoRV) was digested with restriction enzymes XhoI and EcoRV and then cloned into the full-length clone pEAVrVBS which was also cut with the same restriction enzymes, to obtain the recombinant plasmid pEAVrVBSMLV(XhoI-EcoRV).

The fragment GH was digested (step 4) with restriction enzymes BamHI and XhoI and then cloned into the plasmid pEAVrVBSMLV (XhoI-EcoRV) which was also digested with the same restriction enzymes, to obtain the recombinant plasmid pEAVrVBSMLV(XhoI-EcoRV&BamHI-XhoI). Following, (step 5) the fragment EF was digested with restriction enzymes BlnI and BamHI and then cloned into the plasmid pEAVrVBSMLV(XhoI-EcoRV&BamHI-XhoI) which was also digested with the same restriction enzymes, to obtain the recombinant plasmid pEAVrVBSMLV(XhoI-EcoRV&BlnI-XhoI). Finally, in step 6, the fragment CD was digested with restriction enzymes EcoRV and BlnI and then cloned into the plasmid pEAVrVBSMLV(XhoI-EcoRV&BlnI-XhoI) which was also cut with the same restriction enzymes, to obtain the full-length clone pEAVrMLV. Following assembly, the EAV MLV cDNA (SEQ ID NO:1) was immediately downstream of a T7 promoter for generation of full-length in vitro transcripts of EAV MLV.

EXAMPLE 2

Once assembly of the full-length clone was complete, its authenticity was confirmed by sequencing. That sequence is

TABLE 1

Primers used for reverse transcription and PCR amplification of the EAV MLV (ARVAC) fragments AB, CD, EF and GH.
Table 1. Primers for RT-PCR amplification of the EAV MLV vaccine strain (ARVACC)

| Fragment | Primers for reverse transcription | Primers for PCR Forward Primer | Reverse Primer | Digested with restriction enzymes |
|---|---|---|---|---|
| Fragment AB | 5'GTCATCATCAGTGAG GGCAG3' (SEQ ID NO: 5) | Primer a GATTAATACGACTCACT ATAGCTCGAAGTGTGTA TGGTG3' (SEQ ID NO: 6) | Primer b CAGCGGCAGTGAT GTAG3' (SEQ ID NO: 7) | XbaI + EcoRV |
| Fragment CD | 5'CCCCCGCGTTTGGTGA ATGC3' (SEQ ID NO: 8) | Primer c 5'TGCTTGTTCCATCTGG TCTG3' (SEQ ID NO: 9) | Primer d 5'TCTCCAGGTCTGT TTCAAGG3' (SEQ ID NO: 10) | EcoRV + Blnl |
| Fragment EF | 5'ACTTCTGTTGAGCTGA GGAG3' (SEQ ID NO: 11) | Primer e 5'ATTAGGAGCATTCTGG GCACC3' (SEQ ID NO: 12) | Primer f 5'ACGCGACTCAGT GTCTCAGG3' (SEQ ID NO: 13) | Blnl + BamHI |
| Fragment GH | 5'GCACTCAGCTAGTAG ACATCCTCGAGTTTTTT TTTTTTTTTTTTGGTT CCTGGGTGGCTAATAAC (SEQ ID NO: 14) | Primer g 5'TATTCTCGTCCGGTAG GTTCG3' (SEQ ID NO: 15) | Primer h 5'GCACTCAGCTAG TAGACATCCTCG3' (SEQ ID NO: 16) | BamHI + XhoI | set forth herein as SEQ ID NO: 1. The cloned virus sequence (EAVrMLV) had 100% nucleotide identity to the master sequence of the parental MLV vaccine strain (GenBank accession no. EU586275).

EXAMPLE 3

Plasmid containing the full-length sequence of the MLV vaccine (pEAVrMLV; SEQ ID NO: 3; GenBank Accession No. FJ798195) was XhoI-linearized and in vitro transcribed (IVT) RNA was generated for electroporation into baby hamster kidney cells (BHK 21; ATCC CCL10) according to published methods (Balasuriya et al., 1999). The electroporated cells were seeded onto culture plates and incubated at 37° C. until complete cytopathic effect (CPE) was observed to confirm infectivity. When 100% CPE was observed the tissue culture fluid was harvested and stored at −80° C.

EXAMPLE 4

Figure 2:
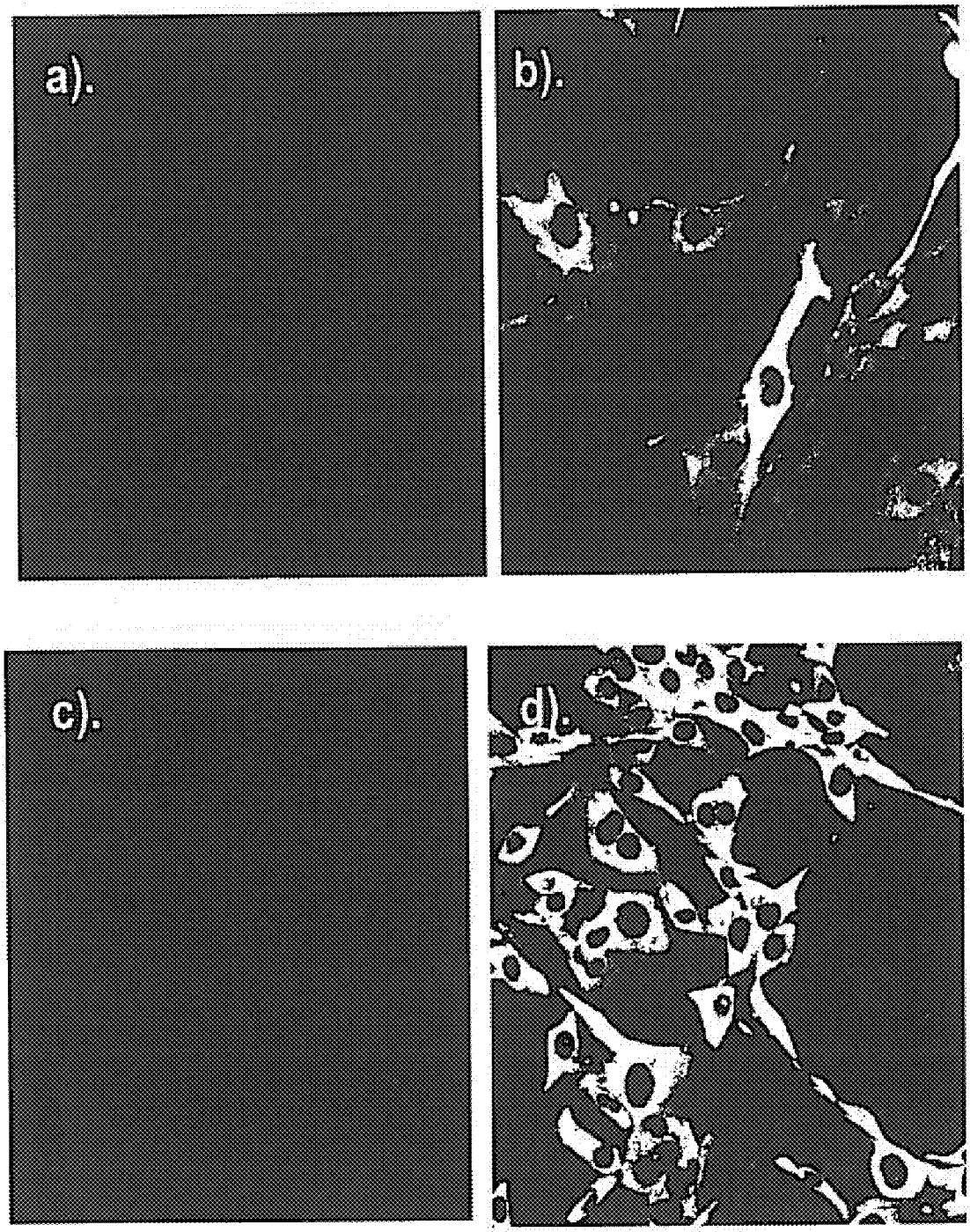
FIG. 2 shows immunofluorescent staining of BHK-21 cells transfected with in vitro transcribed RNA from the cDNA clone shown in FIG. 1.

The infectivity of the IVT RNA was confirmed also by indirect immunofluorescence (IFA; FIG. 2; see Balasuriya et al., 2007) to detect viral protein synthesis in BHK-21 cells transfected with synthetic full-length RNA. Electroporated cells were plated directly onto chamber slides and incubated. The cells were labeled with anti-nsp1 monoclonal antibody 12A1 (Mab; FIG. 2b) and anti-nucleocapsid MAb 3E2 (FIG. 2d) at 24 hours post transfection. Mock-transfected cells were also stained with the same MAbs as controls (FIG. 2a, c).

EXAMPLE 5

To distinguish the cloned virus from the parental strain and from other field and laboratory EAV strains, a silent point mutation (bp12,423 C→G) was introduced into the cDNA clone described in Example 1, providing another infectious cDNA clone termed pEAVrMLVB (SEQ ID NO:4; GenBank Accession No.: FJ798196). The silent point mutation was introduced using QuikChange II site-directed mutagenesis kit (Stratagene) and the mutagenesis primers EAV12423Pmut (5'-GATGCGGGTCCGGAAACCGC-CCGCG-3': SEQ ID NO: 17) and EAV12423Nmut (5'-CGCGGGCGGTTTCCGGACCCATC-3': SEQ ID NO:18). This clone contained a unique restriction site Bsp EI (5'-TCCGGA-3') at positions 12.419-12,424. This restriction site is lacking in pEAVrMLV.

EXAMPLE 6

A vaccine is formulated according to conventional methods, incorporating virus, plasmid, or other vectors comprising SEQ ID NO:1 and including acceptable carriers, including standard buffers, stabilizers, diluents, preservatives, and the like, and may be formulated for extended release. Adjuvants or other immunomodulators may be included, such as Freund's complete or incomplete adjuvants and the like. An effective dosage of vaccine can be determined conventionally by methods known to the skilled artisan, such as administering sequentially increasing doses of virus, plasmid, or vector comprising SEQ ID NO:1 and other additives as described to ascertain proper dosages and any side effects. Single or multiple administrations of vaccine are contemplated. Immune response to the vaccine is monitored by conventional methods, such as seroconversion and antibody titer post-vaccination.

EXAMPLE 7

A marker vaccine is formulated according to conventional methods, incorporating virus, plasmid, or other vectors comprising SEQ ID NO:2 and including acceptable carriers, including standard buffers, stabilizers, diluents, preservatives, and the like, and may be formulated for extended release. Adjuvants or other immunomodulators may be included, such as Freund's complete and incomplete adjuvant and the like. An effective amount of vaccine can be determined conventionally by methods known to the skilled artisan, such as administering sequentially increasing doses of virus, plasmid, or vector comprising SEQ ID NO:1 and other additives as described to ascertain proper dosages and any side effects. Single or multiple administrations of vaccine are contemplated. Immune response to the vaccine is monitored by conventional methods, such as seroconversion and antibody titer post-vaccination. The presence of the marker vaccine is detected by the presence of the unique restriction site Bsp EI (Example 5). This allows monitoring successful vaccination, even in the presence of antibody to wild-type Equine arteritis virus. Even more, it is possible to differentiate vaccinated animals (by the described marker vaccine) from experimentally or naturally infected animals by detecting the mutation.

One of ordinary skill in the art will recognize that additional embodiments of the invention are also possible without departing from the teachings herein. For example, the skilled artisan will appreciate that it is now possible, using the described cDNA clone of the modified live virus of Equine arteritis virus, to provide a validated repository of seed virus for live virus vaccine production, ensuring a genetically homogenous virus stock. Further, the clone finds utility in development of mutations such as disable infectious single cycle (DISC) mutant, allowing a combination of the safety of inactivated vaccines with the immunogenic activity of live viral vaccines. Still further, the cDNA marker clone (SEQ ID NO:4; Example 5) allows development of not only marker vaccines (Example 7), but also diagnostic assays for differentiation of vaccinated animals from naturally infected animals.

This detailed description, and particularly the specific details of the exemplary embodiments, is given primarily for clarity of understanding, and no unnecessary limitations are to be imported, for modifications will become obvious to those skilled in the art upon reading this disclosure and may be made without departing from the spirit or scope of the invention. Relatively apparent modifications, of course, include combining the various features of one or more figures or examples with the features of one or more of other figures or examples.

REFERENCES

Cavanagh, D. 1997. Nidovirales: a new order comprising Coronaviridae and Arteriviridae. *Archives of Virology* 142: 629-633.

Doll, E. R., Bryans, J. T., McCollum, W. H. and Crowe, M. E. W. 1957a. Isolation of a filterable agent causing arteritis of horses and abortion by mares. Its differentiation from the equine abortion (influenza) virus. *Cornell Vet.* 47: 3-41.

Doll, E. R., Knappenberger, R. E., and Bryans, J. T. 1957b. An outbreak of abortion caused by the equine arteritis virus. *Cornell Vet.* 47: 69-75.

Golnik, W., Michalska, Z., and Michalak, T. 1981. Natural equine viral arteritis in foals. *Schweizer Archiv für Tierheilkunde* 123: 523-533.

Timoncy, P. J., McCollum, W. H., Roberts, A. W., and Murphy, T. W. 1986. Demonstration of the carrier state in naturally acquired equine arteritis virus infection in the stallion. *Res. Vet. Sci.* 41: 279-280.

Timoney. P. J., McCollum, W. H., Murphy, T. W., Roberts, A. W., Willard, J. G., and Carswell, G. D. 1987. The carrier state in equine arteritis virus infection in the stallion with specific emphasis on the venereal mode of virus transmission. *J. Reprod. & Fertility Supplementum* 35: 95-102.

Timoney, P. J., McCollum, W. H. and Murphy, T. W. 1992. A longitudinal study of equine arteritis virus infection in standard bred stallions with special reference to occurrence of the carrier state. In: *Proceedings of the Sixth International Conference on Equine Infectious Diseases, Cambridge,* 1991, pp. 231-237.

Calman, S., Rae, C., and Dubovi, E. J. 1988. Equine arteritis virus isolated from a standard bred foal with pneumonia. *Canadian Vet. J.* 29: 937.

Vaala, W. E., Hamir, A. N., Dubovi, E. J., Timoney, P. J., and Ruiz, B. 1992. Fatal, congenitally acquired infection with equine arteritis virus in a neonatal thoroughbred. *Equine Vet. J.* 24: 155-158.

Del Piero, F., Lopez, J., Glaser, A. L. Dubovi, E. J., Schlafer, D., Wilkins, P. and Lein, D. 1995. Histopathology and immunoperoxidase histochemistry of equine arteritis virus in newborn foals: a retrospective study of formalin fixed tissue from natural cases. *Vet. Patrol.* 32, 565.

Del Piero, F., Wilkins, P. A., Lopez, J., W., Glaser, A. L., Dubovi, E. J., Schlafer, D. H., and Lein, D. H. 1997. Equine viral arteritis in newborn foals: clinical, pathological, serological, microbiological and immunohistochemical observations. *Equine Vet. J.* 29: 178-185.

Timoney, P. J. and McCollum, W. H. 1993. Equine viral arteritis. *Veterinary Clinics of North America Equine Practice* 9: 54-59.

Glaser, A. L., Rottier, P. J. M., Horzinek, M. C., and Colenbrander, B. 1996. Equine arteritis virus: a review of clinical features and management aspects. *Vet. Quarterly* 18: 95-99.

Collins, J. K., Kari, S., Ralston, S. L., Bennet, D. G., Traub-Dargatz, J. L., and McKinnon. A. O. 1987. Equine viral arteritis in a veterinary teaching hospital. *Preventative Vet. Med* 4: 389-397.

Timoney, P. J. and McCollum, W. H. 1988. Equine viral arteritis: epidemiology and control. *J. Equine Vet. Sci.* 9: 54-59.

Hedges, J. F., Balasuriya, U. B. R., Timoney, P. J., McCollum, W. H. and MacLachlan, N. J. 1999. Genetic divergence with emergence of phenotypic variants of equine arteritis virus during persistent infection of stallions. *J. Virol.* 73: 3672-3681.

Snijder, E. J., and Meulenberg, J. J. (1998). The molecular biology of *arteriviruses. J Gen Virol* 79 (Pt 5), 961-79.

Snijder, E. J., van Tol, H., Pedersen, K. W., Raamsman, M. J., and de Vries, A. A. (1999). Identification of a novel structural protein of *arteriviruses. J Virol* 73(8), 6335-45.

de Vries, A. A. F., Horzinek, M. C., Rottier, P. J. M., and de Groot, R. J. 1997. The genome organization of the Nidovirales: similarities and differences between arteri-, toro- and coronaviruses. *Seminars in Virology* 8: 33-47.

Snijder, E. J., and Spaan, W. J. (2006). "*Arteriviruses.*" 5th ed. Fields Virology (D. M. Knipe, and Howley, P. M., Ed.) Lippincott Williams & Wilkins, Philadelphia, pp 1337-1355.

de Vries, A. A. F., Chirmside, E. D., Horzinek, M. C., and Rottier, P. J. M. 1992. Structural proteins of equine arteritis virus. *J. Virol.* 66: 6294-6303.

Wiering a, R., A. A. de Vries, M. J. Raamsman, and P. J. Rottier. 2002. Characterization of two new structural glycoproteins, GP(3) and GP(4), of equine arteritis virus. J Virol 76:10829-40.

Moore, 1986. Development and Evolution of Three Equine Vaccines. Irish Vet. J. 40: 105-107.

Balasuriya, U. B. R., Snijder, E. J., Heidner, H. W., Zhang, J., Zevenhoven-Dobbe, J. C.; Boone, J. D., McCollum, W. H., Tinoney, P. J., and MacLachlan, N. J. 2007. Development and characterization of an infectious cDNA clone of the virulent Bucymus strain of Equine arteritis virus. *J. Gen. Virol.* 88: 918-924.

McKnight, K. L., Simpson, D. A., Lin, S. C., Knott, T. A., Polo, J. M., Pence, D. F., Johannsen, D. B., Heidner, H. W., Davis, N. L., and Johnston, R. E. 1996. Deduced consensus sequence of Sindbis virus strain AR339; mutations contained in laboratory strains which affect cell culture and in vivo phenotypes. *J. Virol.* 70: 1981-1989.

Balasuriya, U. B., Snijder, E. J., van Dinten, L. C., Heidner, H. W., Wilson, W. D., Hedges, J. F., Hullinger, P. J., and MacLachlan, N. J. 1999. Equine arteritis virus derived from an infectious cDNA clone is attenuated and genetically stable in infected stallions. *Virology* 260: 201-208.

What is claimed is:

1. An isolated polynucleotide molecule comprising a DNA sequence encoding an infectious RNA molecule encoding a modified live viral strain of an Equine arteritis virus, wherein said DNA sequence is SEQ ID NO:1.

2. An isolated transformed or transfected host cell comprising the DNA sequence of claim 1.

3. A plasmid vector comprising the isolated polynucleotide molecule of claim 1 operatively linked to a suitable promoter.

4. The vector of claim 3, consisting of SEQ ID NO: 3.

5. An isolated infectious RNA molecule encoded by the isolated polynucleotide molecule of claim 1, wherein the infectious RNA molecule encodes a modified live viral strain of an Equine arteritis virus.

6. An isolated polynucleotide molecule comprising a DNA sequence encoding an infectious RNA molecule encoding a modified live viral strain of an Equine arteritis virus, wherein the DNA sequence is SEQ ID NO:2.

7. An isolated transformed or transfected host cell comprising the DNA sequence of claim 6.

8. A plasmid vector comprising the isolated polynucleotide molecule of claim 6 operatively linked to a suitable promoter.

9. An isolated infectious RNA molecule encoded by the isolated polynucleotide molecule of claim 6, wherein the infectious RNA molecule encodes a modified live viral strain of an Equine arteritis virus.

* * * * *